US011167034B2

(12) United States Patent
Jackson et al.

(10) Patent No.: US 11,167,034 B2
(45) Date of Patent: Nov. 9, 2021

(54) POLYMERIC PASTE COMPOSITIONS FOR DRUG DELIVERY

(71) Applicant: The University of British Columbia, Vancouver (CA)

(72) Inventors: John K. Jackson, West Vancouver (CA); Martin E. Gleave, Vancouver (CA); Veronika Schmitt, Vancouver (CA); Claudia Kesch, Essen (DE)

(73) Assignee: The University of British Columbia, Vancouver (CA)

( * ) Notice: Subject to any disclaimer, the term of this patent is extended or adjusted under 35 U.S.C. 154(b) by 0 days.

(21) Appl. No.: 16/619,427

(22) PCT Filed: Jun. 13, 2018

(86) PCT No.: PCT/CA2018/050714
§ 371 (c)(1),
(2) Date: Dec. 4, 2019

(87) PCT Pub. No.: WO2018/227293
PCT Pub. Date: Dec. 20, 2018

(65) Prior Publication Data
US 2020/0147223 A1 May 14, 2020

Related U.S. Application Data

(60) Provisional application No. 62/518,800, filed on Jun. 13, 2017.

(51) Int. Cl.
*A61K 47/34* (2017.01)
*A61K 9/06* (2006.01)
*A61K 47/10* (2017.01)

(52) U.S. Cl.
CPC .............. *A61K 47/34* (2013.01); *A61K 9/06* (2013.01); *A61K 47/10* (2013.01)

(58) Field of Classification Search
CPC .......... A61K 47/34; A61K 47/10; A61K 9/06
See application file for complete search history.

(56) References Cited

U.S. PATENT DOCUMENTS

| | | | |
|---|---|---|---|
| 6,187,640 B1 | 2/2001 | Shimada et al. | |
| 6,193,991 B1 | 2/2001 | Shukla | |
| 6,217,911 B1 | 4/2001 | Vaugn et al. | |
| 6,349,306 B1 | 2/2002 | Malik et al. | |
| 6,451,335 B1 | 9/2002 | Goldenheim et al. | |
| 6,623,729 B2 | 9/2003 | Park et al. | |
| 6,913,760 B2 | 7/2005 | Carr et al. | |
| 6,916,788 B2 * | 7/2005 | Seo ......................... A61P 29/00 424/85.2 | |
| 7,368,126 B2 | 5/2008 | Chen et al. | |
| 7,875,677 B2 | 1/2011 | Jackson et al. | |
| 8,647,657 B2 | 2/2014 | Gibson et al. | |
| 8,846,068 B2 | 9/2014 | Wohabrebbi et al. | |
| 9,265,836 B2 | 2/2016 | Shih et al. | |
| 9,375,420 B2 | 6/2016 | King | |
| 9,549,920 B2 | 1/2017 | Wohabrebbi et al. | |
| 9,744,124 B2 | 8/2017 | Drapeau et al. | |
| 2012/0142649 A1 | 6/2012 | Gray et al. | |
| 2016/0089335 A1 | 3/2016 | Ohri et al. | |

FOREIGN PATENT DOCUMENTS

| | | | |
|---|---|---|---|
| WO | WO 199710849 | 3/1997 | |
| WO | WO200112718 | 2/2001 | |
| WO | WO 200145742 | 6/2001 | |
| WO | WO 2005/002625 A2 * | 1/2005 | ............. A61K 47/34 |
| WO | WO 2005002625 | 1/2005 | |
| WO | WO2005040247 | 5/2005 | |
| WO | WO 2005120595 | 12/2005 | |

OTHER PUBLICATIONS

Rahman (2013) "Adjuvant Chemotherapy for Brain Tumors Delivered via a Novel Intra-Cavity Moldable Polymer Matrix", Plos One 8(10):1-12.
Cabral & Kataoka, (2014) "Progress of drug-loaded polymeric micelles into clinical studies," Journal of Controlled Release 190: 465-476.
Cheng et al., (2007) "Formulation of Functionalized PLGA-PEG Nanoparticles for In Vivo Targeted Drug Delivery," Biomaterials, 28(5): 869-876.
Hines & Kaplan et al., (2013) "Poly (lactic-co-glycolic acid) controlled release systems experimental and modeling insights," NIH, Crit Rev Ther Drug Carrier Syst, 30(3): 257-276.
Huang et al., (2013) "The influence of additives in modulating drug delivery and degradation of PLGA thin films," NPG Asia Materials, 5,e54:1-11.
Jackson et al.; (2004) "The characterization of novel polymeric paste formulations for intratumoral delivery," International Journal of Pharmaceutics, 270: 185-198.
Jackson et al.; (2004) "Characterization of perivascular poly(lactic-co-glycolic acid) films containing paclitaxel," International Journal of Pharmaceutics, 283: 97-109.
Jackson et al., (2007) "The characterization of paclitaxel-loaded microspheres manufactured from blends of poly (lactic-co-glycolic acid) (PLGA) and low molecular weight deblock copolymers," International Journal of Pharmaceutics, 342: 6-17.
Jackson et al.: (2000) "The Suppression of Human Prostate Tumor Growth in Mice by the Intratumoral Injection of a Slow-Release Polymeric Paste Formulation of Paclitaxel," Cancer Research, 60: 4146-4151.
Jain (2000) "The manufacturing techniques of various drug loaded biodegradable poly(lactide-co-glycolide (PLGA) devices," Biomaterials, 21: 2475-2490.

(Continued)

*Primary Examiner* — Pancham Bakshi
(74) *Attorney, Agent, or Firm* — Rudy J. Ng; Bozicevic, Field & Francis LLP

(57) ABSTRACT

This invention provides compositions for controlled localized release of one or more drugs within a subject. More particularly, described herein are compositions comprising a hydrophobic water-insoluble polymer, a low molecular weight biocompatible glycol, and one or more drugs. The compositions described herein may also optionally include a di-block copolymer and/or a swelling agent.

18 Claims, 19 Drawing Sheets

(56) References Cited

OTHER PUBLICATIONS

Kamaly et al.; (2016) "Degradable Controlled-Release Polymers and Polymeric Nanoparticles: Mechanisms of Controlling Drug Release," Chem Rev., 116(4): 2602-2663.
Makadia (2011) "Poly Lactic-co-Glycolic Acid (PLGA) as Biodegradable Controlled Drug Delivery Carrier," Polymers, 3: 1377-1397.
Matsumura et al.; (2004) "Phase 1 Clinical and pharmacokinetic evaluation of NK911 a micelle-encapsulated doxorubicin," British Journal of Cancer, 91, 1775-1781.
Pakulska et al.; (2016) "Encapsulation-free controlled release: Electrostatic adsorption eliminates the need for protein encapsulation in PLGA nanoparticles," Sci. Adv. 2: 1-10.
Pereira et al.; (2016)"Influence of PLGA and PLGA-PEG on the dissolution profile of oxaliplatin," 26(2): 1-7.
Siegel et al.; (2006) "Effect of drug type on the degradation rate of PLGA matrices," European Journal of Pharmaceutics and Biopharmaceutics 64: 287-293.
Winternitz (1996) "Development of a Polymeric Surgical Paste Formulation for Taxol," Pharmaceutical Research, 13(3) 368-375.
Yokoyama et al.; (1991) "Toxicity and Antitumor Activity against Solid Tumors of Micelle-forming Polymeric Anticancer Drug and Its Extremely Long Circulation in Blood," Cancer Research, 51: 3229-3236.
Yoo et al.; (2001) "Biodegradable polymeric micelles composed of doxorubicin conjugated PLGA-PEG block copolymer," Journal of Controlled Release, 70: 63-70.
Zhang et al.; (1996) "Determination of surfactant critical micelle concentration by a novel fluorescence depolarization technique," J. Biochem. Biophys. Methods, 31: 145-150.
Zhang et al.; (1996) "Development of amphiphilic deblock copolymers micellar carriers of taxol," International Journal of Pharmaceutics, 132: 195-206.

* cited by examiner

--X-- 50% PEG:31% PLGA:19% Diblock, 4% VPC-27
--▲-- 50% PEG:31% PLGA:19% Diblock, 4% Bicalutamide
—●— 50% PEG:31% PLGA:19% Diblock, 0.5% Docetaxel --X-- 50% PEG:25% PLGA:25% Diblock, 4% VPC-27
--▲-- 50% PEG:25% PLGA:25% Diblock, 4% Bicalutamide
—●— 50% PEG:25% PLGA:25% Diblock, 0.5% Docetaxel --○-- 63% PEG:37% PLGA, Docetaxel 4 %
—●— 76% PEG:24% PLGA, Docetaxel 4 %

--△-- 63% PEG:37% PLGA, Bicalutamide 4 %
—▲— 76% PEG:24% PLGA, Bicalutamide 4 %

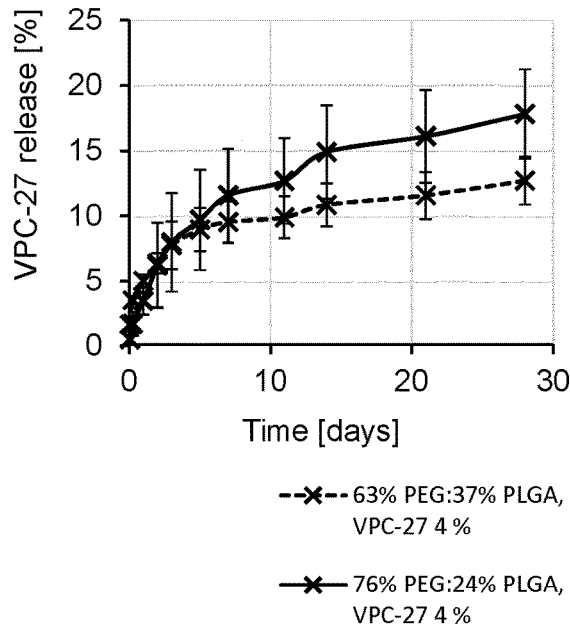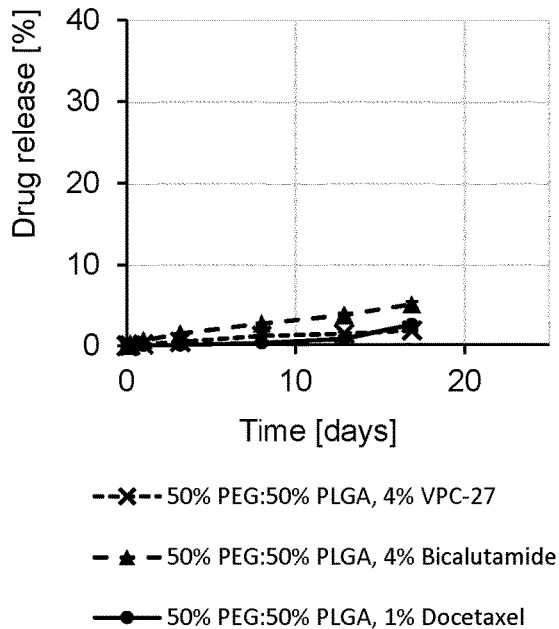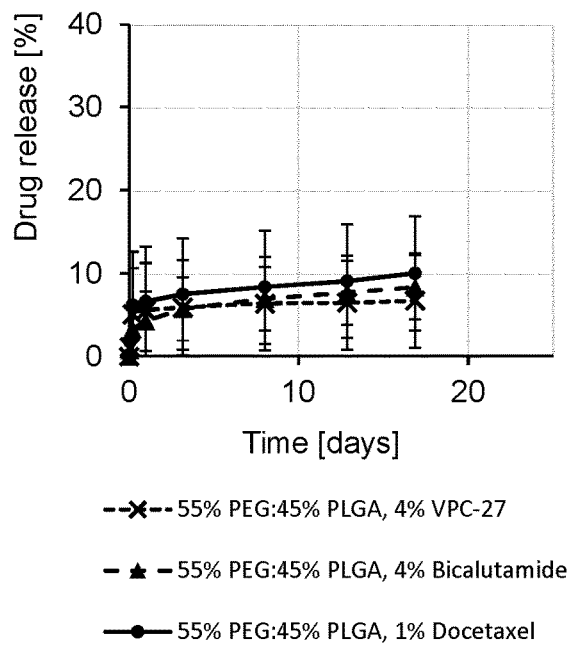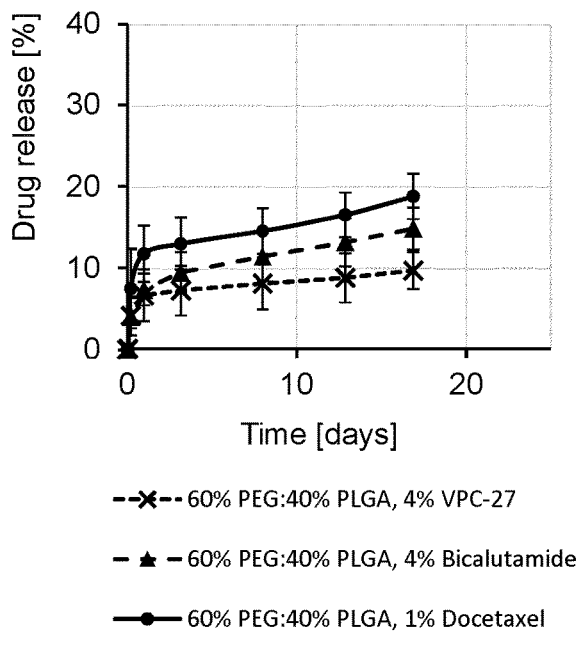

POLYMERIC PASTE COMPOSITIONS FOR DRUG DELIVERY

CROSS REFERENCE TO RELATED APPLICATIONS

This application claims the benefit of U.S. Provisional Patent Application Ser. No. 62/518,800 filed on 13 Jun. 2017, entitled "POLYMERIC PASTES FOR DRUG DELIVERY".

FIELD OF THE INVENTION

This invention relates to biodegradable polymeric pastes suitable for drug delivery. More particularly, the invention relates to injectable polymeric pastes that release drugs in a controlled manner.

BACKGROUND OF THE INVENTION

Prostate Cancer

The anatomy and pathogenesis of prostate cancer (PCa) lends itself to localized treatment modalities. Low risk early-stage localized PCa often has a low long-term likelihood of progression and metastases, and treatments such as surgery or radiation may unnecessarily expose patients to the risks of treatment without a concomitant meaningful cancer-specific benefit. While surgery and radiation lead to excellent long-term cancer-free rates, it is estimated that PCa-related death will be prevented in only one out of 5 to 48 patients undergoing treatment[1,2]. To minimize the risk of 'overtreatment', active surveillance (AS) without immediate treatment has become an increasingly utilized option for some men with appropriate low to intermediate-risk cancer characteristics.

Large population-based studies evaluating outcomes for PCa based on clinical and pathological parameters have established well defined PCa risk categories[3]. Low risk PCa, defined as cT1-cT2a, Gleason score≤6, PSA<10, is unlikely to progress and require radical treatment, and is readily amenable to AS. AS for low and low-tier intermediate risk PCa has demonstrated favourable outcomes, and can spare up to 50% of men from radical treatment at 5 years[4]. AS has provided insight into the natural history of lower risk PCa and also addresses the population health concerns arising from PCa over-detection and overtreatment. Triggers to come off AS and proceed to definitive intervention include rises in serum PSA values, histological progression on biopsy, development of lower urinary tract symptoms, or patient anxiety on follow up.

While AS aims to minimize the risk of overtreatment, it relies on the assumption that the cancer will not metastasize and requires biopsies every 1-2 years. Taking this strategy can cause anxiety over living with an untreated cancer and leads to delayed whole-gland treatment (radiation or surgery) in 30-40% of patients[5]. For some men with low-risk and intermediate-risk PCa, AS may be undesirable, yet the short-term and long-term complications associated with surgery and radiation present unacceptable risks. Moreover, any benefits of curative treatment with surgery or radiotherapy are small at durations of follow up of less than 10 years, and are hence associated with adverse effects on quality of life without near-term benefits in disease control[6,7].

For this reason, there has been a growing interest in minimally invasive focal therapies for PCa[8-10]. The dual goals are to eradicate a focal area of cancer and maintain normal urinary, sexual, and bowel function. Several minimally invasive ablation methods, such as cryotherapy[11,12] and high-intensity focused ultrasound (HIFU)[13], have been developed and are currently FDA approved. These are, however, ablative therapies that kill benign and cancer cells indiscriminately and can lead to erectile dysfunction and fistulae.

Upper Tract Urothelial Carcinoma

Urothelial carcinomas (UCs) may occur in the lower urinary zones (bladder or urethra) or in the upper urinary tract (UUT: pyelocaliceal cavities and ureter)[14]. Over 90% of UCs are located in the bladder with under 10% occurring in the upper tract (UTC). Patients with bladder cancer are usually diagnosed with early stage disease and the cancer confined to the superficial urothelium. This is partly due to the easy access of diagnostic equipment via the urethra. However, many patients with UTCs are not diagnosed early and may have already progressed to invasive disease. Staging of UTCs may also be difficult as the tissue is fragile with only limited musculature so that biopsies do not always accurately describe the disease level.

Once diagnosed, radical nephroureterectomy (RNU) with bladder-cuff removal is considered the standard treatment of UTC[15,16]. This procedure involves full removal of the kidney, the ureter and the bladder cuff. Tumor cell spillage may be a problem with such procedures. Furthermore, many patients are not candidates for this treatment. Some patients with low-risk disease, may be offered a more conservative treatment such as endoscopic ablation or segmental removal[14]. Clearly, with later diagnosis, the prognosis for these patients with UTC is poor. Chemotherapeutic options are limited for these patients especially because cisplatin based regimens are associated with nephrotoxicity, which may be exacerbated, when one kidney is removed. Other drugs used to treat bladder cancer such as Mitomycin C and Gemcitabine may have a preferred toxicity profile. However, when used to treat bladder cancer these drugs may be delivered at high concentrations intravesically (directly into the bladder) so that a 2 hour retention allows reasonable drug uptake into the tissues after tumor resection. More recently, the drug docetaxel is under investigation as a chemotherapeutic option to treat bladder cancer locally and UTC by systemic delivery. The combination of gemcitabine and docetaxel, is also being studied as an improvement to using either drug alone[17].

Because the UUT tissues cannot be treated locally with a drug solution (the pelvis is accessible but drug solutions would quickly wash into the bladder) one company (Urogen™) has developed a gel formulation of mitomycin called Mitogel. This gel undergoes a thermos-reversible gel transition in the body so may be injected as a liquid to form a semi solid gel in the pelvis of the kidney. The pluronic-based gel dissolves slowly, but allows for some retention of the drug in the tissues at the target site.

Background Chronic Scrotal Pain

Chronic scrotal contents pain (CSCP) is a common entity afflicting men of all ages and has been reported to peak in the mid to late thirties[18,19]. A study conducted in Switzerland reported an estimated incidence of 350-400 cases per 100,000 men per year[20]. CSCP is an intermittent or constant, unilateral or bilateral pain involving the testes, epididymis, vas deferens or para-testicular structures of at least three months duration[21]. The etiology for CSCP is varied and is divided into scrotal and extra-scrotal causes. Extra-scrotal causes involve irritation of the ilioinguinal, genitofemoral or pudendal nerves. This can include inguinal hernias/hernia repairs, urolithiasis, or retroperitoneal tumors among many others. Causes within the scrotum include infection, prior scrotal surgery, post vasectomy pain or anatomic abnormalities.

Effective treatment options for CSCP are limited and data consists primarily of non-randomized, small studies. Conservative therapies include rest, ice and scrotal supports along with pain education and counselling. There is no standardized protocol for treatment[21], but the mainstay of medical therapy involves nonsteroidal anti-inflammatory drugs (NSAIDs) with tricyclic antidepressants or gabapentin as alternatives[22]. Antibiotics may be trialed, if epididymoorchitis is in the differential diagnosis. Beyond this, noninvasive options include pelvic floor physiotherapy, acupuncture or transcutaneous electrical nerve stimulation (TENS), but these are not associated with frequent or durable control of CSCP. Lidocaine combined with steroid injections short term relief for men with testicular pain[23]. A case report from 2009 indicated success with sacral nerve stimulation though no further studies have validated this response[24]. In 2012 a case series reported on treatment of chronic orchialgia using pulsed radiofrequency ablation, but again are not associated with frequent or durable control[25]. An open-label trial from 2014 on spermatic cord injections with Botulinum toxin showed modest results for up to 3 months, but with limited effect at six-month follow up[26]. A very recent study reported that a subset of men with chronic testicular pain can benefit from excess doses of vitamin B12 and testosterone, but this type of treatment may be associated with increased risk of prostate cancer associated with testosterone treatment[27].

Surgical management is reserved for those who have persistent scrotal pain despite adequate trials of conservative and medical therapies. In the past, surgery for scrotal pain has focused on the area of the scrotum thought to be the source of pain. Epididymectomy, vasovasostomy, varicocelectomy and orchiectomy have all been attempted, but are invasive, associated with risk of loss of the testicle, and have low long-term pain control. In a study by Polackwich et al., vasovasostomy or vasoepididymostomy, in men with post vasectomy pain syndrome, provided a degree of relief in 82% of patients[28]. Epididymectomy for post vasectomy pain was studied by Hori et al. and produced a mean decrease in pain score by 67%[29]. Epididymectomy for epididymal pain led to significant reductions in pain which were more pronounced for epididymal cysts compared to chronic epididymitis[30].

In contrast to anatomically based surgical interventions, microsurgical spermatic cord denervation (MSCD) provides effective pain relief for multiple sources of intrascrotal pain in men who respond to initial spermatic cord block. Multiple studies have shown results for MSCD with complete response rates in approximately 70 percent of patients (range 49-96%)[31-35]. MSCD can be utilized as an initial surgical management tool or after other surgical interventions have failed[36]. As with other surgical procedures, MSCD does involve use of a general anesthetic and there are risks of testicular atrophy or loss of testicle, as well as persistent pain despite and expensive surgical procedure.

Overall, the treatment of CSCP is challenging due to its multifaceted etiology and indistinct presentation, which imposes a significant burden on the patient and physician. Many patients with CSCP are left with untreated pain, seeking consultation with multiple physicians, loss of work, and risk of narcotic exposure[31]. As highlighted in the European Urological Association 2013 guidelines, chronic scrotal pain is "often associated with negative cognitive, behavioural, sexual or emotional consequences."[37]. A study from 2011 found that men with orchialgia had decreased scores in orgasmic function, intercourse satisfaction and sexual desire compared to men with no pain. Overall sexual satisfaction and International Index of Erectile Function scores were also significantly lower in this group[38]. Thus, there remains an unmet clinical need for effective delivery of therapeutics in the management of CSCP.

To provide pain relief for CSCP, spermatic cord block is a valuable treatment option. The single local injection of lidocaine to break the pain cycle[39] is suggested at a dose of 100 mg (10 mL of 1% lidocaine) for peripheral nerve block[40]. This regional delivery of lidocaine is characterized by a quick onset (3 min) and of short duration (60-120 min). A maximum dose of 4.5 mg/kg of lidocaine alone can be used and if epinephrine is added this amount can be further increased to 6 mg/kg. Epinephrine acts as a vasoconstrictor, slows the systemic absorption of lidocaine and prolongs its duration of action[41,42].

Instead of using epinephrine, which produces the common unwanted sympathomimetic side effects including vasoconstriction and reduced blood flow, it is preferred to use a drug carrier for lidocaine, which resides locally and releases small amounts of the drug over a more extended period of time.

In traditional chemotherapy, drugs are delivered systemically following resection surgery or to treat metastatic disease. However, to treat local tumors, a better method might be to deliver a controlled release drug formulation to the disease site. Currently, there are few such formulations available, often because the target tissue is difficult to access and locally delivered solutions of drugs are cleared rather quickly from the area, offering little efficacy. Certain tissues (like the prostate or upper urothelial tract) are routinely accessed in patients (needle biopsy for prostate or by endoscopy for UUT) and offer potential sites for local drug delivery. For the prostate, where the target tissue is confined to an organ with defined boundaries, an injectable, slow release polymeric paste might be suitable. Delivering drugs directly to the pelvis of the kidney to treat UTC is problematic because the ureter cannot be blocked by a polymeric paste for a long time. Delivery to this area may require using an injectable that breaks up or dissolves over a reduced time-frame so that urine may flow but some the drug loaded formulations remains to allow for local tissue uptake.

Injectable Polymeric Paste

Drugs are normally delivered orally or by injection to allow systemic uptake and circulation to most parts of the body. For many drugs this route of administration is ideally suited, for example, insulin for diabetes or statins for heart disease. However, many diseases are localized and the preferred method is to deliver the drug directly to the site of action. For example, painkillers for chronic localized pain, anticancer drugs for local tumors and anti-arthritic drugs to relieve symptoms of arthritis and joint pain. Accordingly, there have been numerous attempts to design locally injectable systems to deliver drugs to specific body sites. This targeted approach may also minimize systemic toxicity often associated with conventional methods of delivering drugs. The intravenous delivery of anticancer drugs often causes severe side effects and systemic toxicities usually limit drug dose. Local polymeric drug delivery systems could mitigate systemic side effects and allow for the delivery of high local doses.

PLGA is a common constituent of polymeric drug delivery systems. It is an FDA-approved biopolymer of lactic acid (D,L-LA) and glycolic acid (GA) and has been used both as a drug delivery carrier and as a scaffold for tissue engineering[43,44]. The degradation of PLGA depends on many factors including, but not limited to, the ratio of LA to GA, crystallinity, weight average molecular weight of the polymer, shape of the matrix, and type and amount of drug incorporated[45,46]. The ratio of LA to GA is a major player in degradation and polymers with a higher amount of the more hydrophilic GA generally degrade faster. The degradation products of PLGA are the hydrolysis products LA and GA. Both can enter the citric acid cycle and can be excreted as water and carbon dioxide, or in the case of GA, mainly excreted unchanged by the kidney[46]. Minor toxicities like transient inflammation have been reported for some PLGA based implants[47], but they likely reflect increased exposure times and reduced clearance of the degradation products.

Injectable, drug loaded polymeric pastes are attractive for local drug delivery because ultrasound or MRI-guided systems allow pinpoint accuracy in directing a needle or catheter system to a target area. Others have described injectable liquids (e.g., Atrigel™)[48] composed of an organic solvent like acetone or polyvinyl-pyrrolidone and a drug that when injected into the body solidified as the solvent dissolved away. Such a system is flawed because introducing an organic solvent into potentially sensitive tissue areas may induce unwanted local toxicity. Local drug delivery systems ranging from drug loaded polymeric coatings of stents, injectable microspheres[49], perivascular films[50] and injectable polymeric pastes have been described[51]. In these examples, the antiproliferative drug paclitaxel was used to inhibit proliferative events associated with restenosis, cancer and arthritis.

An early polymeric paste system described in the literature was based on a blend of polycaprolactone and methoxypolyethylene glycol that was injectable (molten) at above body temperatures, but set to an implant at 37° C. to release drug[52]. The implant was brittle and hard and the high temperature delivery was inappropriate for the injection into sensitive locations. Injectable paclitaxel-loaded polymeric paste made from a mixture of a triblock copolymer and methoxypolyethylene glycol that was injectable at room temperature and formed a solid implant in vivo has also been described[51]. This paste performed poorly in so far as the release rate of the drug paclitaxel and other hydrophobic drugs was too slow to achieve adequate tissue levels of active drug and the degradation profile of the polymer was too long potentially interfering with re-treatment injections. The inclusion of diblock copolymers of various compositions in solid (not paste) microspheres has been previously described[49]. In this case, the dissolution of the diblock from the microspheres allowed for increased hydrophobic drug release as well as opening of the matrix to water and enhanced degradation. Microsphere formulations are quite different to pastes. They do not flow under injection so must be injected in a liquid suspension. As such, they can disperse easily from a targeted tissue area.

SUMMARY OF THE INVENTION

This invention relates to improved polymeric pastes for controlled drug delivery. The compositions described herein allow for the formulation and injection of paste mixtures into the body of a subject whereby the paste mixture may form an implant at a localized site. In one aspect, the present invention provides for controlled drug release from polymeric paste delivery systems by using selected low-viscosity water-insoluble polymers to adjust the viscosity of the paste formulation and regulate release rates of drug(s) payload. The paste may be manufactured from simple polymers that form soft-hydrogel-like implants, which may degrade quickly where needed and the release of the drug and/or drug combinations may be controlled. This invention is based on the surprising discovery that only defined ratios and compositions of PEG and PLGA can be used effectively to form a waxy drug delivery deposit in vivo. Furthermore, it was discovered that the addition of a diblock copolymer may further control the release or fine tune the release of drug from the composition in situ.

Provided herein are non-solvent based, biodegradable polymeric pastes with controlled drug release properties. Furthermore, some of the paste compositions described herein have a low enough viscosity for injection, but set in vivo to a more solid formulation to allow controlled release by drug diffusion. Alternatively, the inclusion of a mucoadhesive swelling agent may further slow down the wash out time of the formulation for bladder uses.

When placed in an aqueous environment such as a body compartment, the low molecular weight biocompatible glycol can dissolve out of the matrix and the hydrophobic water-insoluble polymer can partially solidify in a semi-hydrated state that renders the implant waxy. The low molecular weight biocompatible glycols used herein are water-soluble polymer, but may not dissolve entirely out of the matrix over the lifetime of the implant, which may result in a waxy form. A further aspect of the invention includes compositions comprising a low molecular weight biocompatible glycol; a hydrophobic water-insoluble polymer; a drug; and optionally, a biocompatible diblock co-polymer such that the composition is a semi-solid at temperatures at or about room temperature and are capable of being injected into a subject through a syringe. This aspect of the invention has the advantage of being soft, comfortable, non-compressing of tissues whilst providing long-term, controlled release of a drug at a specific site of injection in a subject.

This invention also provides methods for using the aforementioned compositions to form implants in vitro and in vivo. In vivo methodologies include injection of the composition to a site in a subject's body where the drug-containing implant is formed.

This invention also provides injection devices containing an implant forming composition according to this invention.

In a first aspect, there is provided a composition, the composition including: (a) a hydrophobic water-insoluble polymer having an inherent viscosity (IV) of about 0.15 to about 0.5 dL/g; (b) a low molecular weight biocompatible glycol; with a molecular weight at or below 1,450 Daltons; and (c) one or more drug compounds or pharmaceutically acceptable salt, solvate or solvate of the salt thereof.

In a further aspect, there is provided a composition, the composition including: (a) a hydrophobic water-insoluble polymer having an inherent viscosity (IV) of about 0.15 to about 0.55 dL/g; (b) a low molecular weight biocompatible glycol; with a molecular weight at or below 1,450 Daltons; and (c) one or more drug compounds or pharmaceutically acceptable salt, solvate or solvate of the salt thereof.

In a further aspect, there is provided a composition, the composition including: (a) a hydrophobic water-insoluble polymer having an inherent viscosity up to and including about 0.55 dL/g; (b) a low molecular weight biocompatible glycol; with a molecular weight at or below 1,450 Daltons; and (c) one or more drug compounds or pharmaceutically acceptable salt, solvate or solvate of the salt thereof.

In a further aspect, there is provided a composition, the composition including: (a) a hydrophobic water-insoluble polymer having an inherent viscosity up to an including about 0.50 dL/g; (b) a low molecular weight biocompatible glycol; with a molecular weight at or below 1,450 Daltons; and (c) one or more drug compounds or pharmaceutically acceptable salt, solvate or solvate of the salt thereof.

In a further aspect, there is provided a composition, the composition including: (a) a hydrophobic water-insoluble polymer having a molecular weight up to and including about 60,000 Daltons; (b) a low molecular weight biocompatible glycol; with a molecular weight at or below 1,450 Daltons; and (c) one or more drug compounds or pharmaceutically acceptable salt, solvate or solvate of the salt thereof.

In a further aspect, there is provided a composition, the composition including: (a) a hydrophobic water-insoluble polymer having a molecular weight up to and including about 76,000 Daltons; (b) a low molecular weight biocompatible glycol; with a molecular weight at or below 1,450 Daltons; and (c) one or more drug compounds or pharmaceutically acceptable salt, solvate or solvate of the salt thereof.

In a further aspect, there is provided a composition, the composition including: (a) a hydrophobic water-insoluble polymer having a molecular weight between about 4,300 daltons and about 60,000 Daltons; (b) a low molecular weight biocompatible glycol; with a molecular weight at or below 1,450 Daltons; and (c) one or more drug compounds or pharmaceutically acceptable salt, solvate or solvate of the salt thereof.

In a further aspect, there is provided a composition, the composition including: (a) a hydrophobic water-insoluble polymer having a molecular weight between about 4,200 daltons and 76,000 Daltons; (b) a low molecular weight biocompatible glycol; with a molecular weight at or below 1,450 Daltons; and (c) one or more drug compounds or pharmaceutically acceptable salt, solvate or solvate of the salt thereof.

In a further aspect, there is provided a composition, the composition including: (a) a hydrophobic water-insoluble polymer having a molecular weight between about 3,200 daltons and 80,000 Daltons; (b) a low molecular weight biocompatible glycol; with a molecular weight at or below 1,450 Daltons; and (c) one or more drug compounds or pharmaceutically acceptable salt, solvate or solvate of the salt thereof.

In a further aspect, there is provided a composition, the composition including: (a) a hydrophobic water-insoluble polymer having a molecular weight between about 2,200 daltons and 76,000 Daltons; (b) a low molecular weight biocompatible glycol; with a molecular weight at or below 1,450 Daltons; and (c) one or more drug compounds or pharmaceutically acceptable salt, solvate or solvate of the salt thereof.

In a further aspect, there is provided a composition, the composition including: (a) a hydrophobic water-insoluble polymer having a molecular weight between about 2,200 daltons and 70,000 Daltons; (b) a low molecular weight biocompatible glycol; with a molecular weight at or below 1,450 Daltons; and (c) one or more drug compounds or pharmaceutically acceptable salt, solvate or solvate of the salt thereof.

In a further aspect, there is provided a composition, the composition including: (a) a hydrophobic water-insoluble polymer having a molecular weight between about 2,200 daltons and 60,000 Daltons; (b) a low molecular weight biocompatible glycol; with a molecular weight at or below 1,450 Daltons; and (c) one or more drug compounds or pharmaceutically acceptable salt, solvate or solvate of the salt thereof.

In a further aspect, there is provided a pharmaceutical composition comprising a compositions as described herein, together with a pharmaceutically acceptable diluent or carrier.

In a further aspect, there is provided a use of a composition as described herein, for the manufacture of a medicament.

In a further aspect, there is provided a use of a composition as described herein, for the treatment of a medical condition for which the drug is used.

In a further aspect, there is provided a composition as described herein, for use in the treatment of a medical condition.

In a further aspect, there is provided a commercial package comprising: (a) composition as described herein; and (b) instructions for the use.

The composition may further include a di-block copolymer. The composition may further include a swelling agent. The composition may further include a di-block copolymer and a swelling agent.

The hydrophobic water-insoluble polymer may have an inherent viscosity (IV) of about 0.15 to about 0.5 dL/g is polylactic-co-glycolic acid (PLGA). The hydrophobic water-insoluble polymer may have an inherent viscosity (IV) of about 0.15 to about 0.25 dL/g is polylactic-co-glycolic acid (PLGA). The hydrophobic water-insoluble polymer may have an inherent viscosity (IV) of about 0.25 to about 0.5 dL/g is polylactic-co-glycolic acid (PLGA). The hydrophobic water-insoluble polymer may have an inherent viscosity (IV) of about 0.15 to about 0.55 dL/g is polylactic-co-glycolic acid (PLGA). The hydrophobic water-insoluble polymer may have an inherent viscosity (IV) of about 0.15 to about 0.60 dL/g is polylactic-co-glycolic acid (PLGA). The hydrophobic water-insoluble polymer may have an inherent viscosity (IV) of about 0.10 to about 0.5 dL/g is polylactic-co-glycolic acid (PLGA). The hydrophobic water-insoluble polymer may have an inherent viscosity (IV) of about 0.10 to about 0.6 dL/g is polylactic-co-glycolic acid (PLGA). The hydrophobic water-insoluble polymer may have an inherent viscosity (IV) of about 0.15 to about 0.45 dL/g is polylactic-co-glycolic acid (PLGA). The hydrophobic water-insoluble polymer may have an inherent viscosity (IV) at of below about 0.3 dL/g is polylactic-co-glycolic acid (PLGA).

The hydrophobic water-insoluble polymer may have a molecular weight between about 2,200 daltons and 70,000 Daltons. The hydrophobic water-insoluble polymer may have a molecular weight between about 4,300 daltons and 60,000 Daltons. The hydrophobic water-insoluble polymer may have a molecular weight between about 4,200 daltons and 60,000 Daltons. The hydrophobic water-insoluble polymer may have a molecular weight between about 4,300 daltons and 70,000 Daltons. The hydrophobic water-insoluble polymer may have a molecular weight between about 4,300 daltons and 75,000 Daltons. The hydrophobic water-insoluble polymer may have a molecular weight between about 4,300 daltons and 50,000 Daltons. The hydrophobic water-insoluble polymer may have a molecular weight between about 3,300 daltons and 60,000 Daltons. The hydrophobic water-insoluble polymer may have a molecular weight between about 2,300 daltons and 60,000 Daltons.

The PLGA may have a ratio of lactic acid (LA):glycolic acid (GA) at or below 75:25. The PLGA may have a ratio of lactic acid (LA):glycolic acid (GA) at or below 65:35. The PLGA may have a ratio of lactic acid (LA):glycolic acid (GA) at or below 50:50. The PLGA may have a ratio of lactic acid (LA):glycolic acid (GA) of between 50:50 and 75:25. The PLGA may have a ratio of lactic acid (LA): glycolic acid (GA) at or below 85:15.

The hydrophobic water-insoluble polymer may have an inherent viscosity (IV) of about 0.15 to about 0.3 dL/g. The hydrophobic water-insoluble polymer may have an inherent viscosity (IV) of about 0.15 to about 0.25 dL/g.

The low molecular weight biocompatible glycol may have a molecular weight between about 76 Daltons and about 1,450 Daltons. The low molecular weight biocompatible glycol may have a molecular weight between about 300 Daltons and about 1,450 Daltons. The low molecular weight biocompatible glycol may have a molecular weight between about 76 Daltons and about 900 Daltons. The low molecular weight biocompatible glycol may have a molecular weight between about 300 Daltons and about 900 Daltons.

The low molecular weight biocompatible glycol may be selected from Polyethylene glycol (PEG), methoxypolyethylene glycol (mePEG) and propylene glycol. The low molecular weight biocompatible glycol may be PEG and mePEG. The PEG or mePEG may have an average molecular weight of between 300 Daltons and 1,450 Daltons.

The composition may include a hydrophobic water-insoluble polymer having an inherent viscosity (IV) of about 0.15 to about 0.5 dL/g is PLGA having a LA:GA ratio of 50:50 and a low molecular weight biocompatible glycol is PEG or mePEG with a molecular weight of about 300 Daltons to about 1,450 Daltons. The composition may include a hydrophobic water-insoluble polymer having an inherent viscosity (IV) of about 0.15 to about 0.5 dL/g is PLGA having a LA:GA ratio of 65:35 and a low molecular weight biocompatible glycol is PEG or mePEG with a molecular weight of about 300 Daltons to about 1,450 Daltons. The composition may include a hydrophobic water-insoluble polymer having an inherent viscosity (IV) of about 0.15 to about 0.5 dL/g is PLGA having a LA:GA ratio of 75:25 and a low molecular weight biocompatible glycol is PEG or mePEG with a molecular weight of about 300 Daltons to about 1,450 Daltons. The composition may include a hydrophobic water-insoluble polymer having an inherent viscosity (IV) of about 0.15 to about 0.5 dL/g is PLGA having a LA:GA ratio at or below 75:25 and a low molecular weight biocompatible glycol is PEG or mePEG with a molecular weight of about 300 Daltons to about 1,450 Daltons. The composition may include a hydrophobic water-insoluble polymer having an inherent viscosity (IV) of about 0.15 to about 0.5 dL/g is PLGA having a LA:GA ratio of 50:50 and a low molecular weight biocompatible glycol is PEG or mePEG with a molecular weight of about 300 Daltons to about 900 Daltons.

The ratio of PEG or mePEG to PLGA may be between about 80%:20% and about 40%:60%. The ratio of PEG or mePEG to PLGA may be between about 70%:30% and about 40%:60%. The ratio of PEG or mePEG to PLGA may be between about 80%:20% and about 50%:50%. The ratio of PEG or mePEG to PLGA may be between about 60%: 40% and about 40%:60%. The ratio of PEG or mePEG to PLGA may be between about 60%:40% and about 50%: 50%.

The low molecular weight biocompatible glycol may be PEG 300. The low molecular weight biocompatible glycol may be PEG 600. The low molecular weight biocompatible glycol may be PEG 900.

The di-block copolymer may be between 13% and 26% of the total paste polymer, wherein the di-block copolymer substitutes for hydrophobic water-insoluble polymer. The di-block copolymer may be between 13% and 26% of the total paste polymer. The di-block copolymer may be between 10% and 30% of the total paste polymer, wherein the di-block copolymer substitutes for hydrophobic water-insoluble polymer. The di-block copolymer may be between 5% and 40% of the total paste polymer, wherein the di-block copolymer substitutes for hydrophobic water-insoluble polymer.

The di-block copolymer may have one hydrophobic monomer and one hydrophilic monomer.

The hydrophilic monomer may be selected from: PEG; and MePEG; and the hydrophobic monomer may be selected from: PLGA; polylactic acid (PLA); Poly-L-lactic Acid (PLLA); and Polycaprolactone (PCL). The hydrophilic monomer may be selected from: PEG; and MePEG; and the hydrophobic monomer may be selected from: polylactic acid (PLA); Poly-L-lactic Acid (PLLA); and Polycaprolactone (PCL). The hydrophilic monomer may be selected from: PEG; and MePEG; and the hydrophobic monomer may be selected from: PLGA; polylactic acid (PLA); and Poly-L-lactic Acid (PLLA). The hydrophilic monomer may be MePEG; and the hydrophobic monomer may be PLGA. The hydrophilic monomer may be PEG; and the hydrophobic monomer may be PLLA. The hydrophilic monomer may be PEG; and the hydrophobic monomer may be PLGA. The di-block copolymer may be amphiphilic. The di-block copolymer may be PLLA-mePEG. The di-block copolymer may be PLLA-PEG. The di-block copolymer may be PLA-mePEG. The di-block copolymer may be PLA-PEG.

The one or more drug compounds or pharmaceutically acceptable salt, solvate or solvate of the salt thereof may be selected from one or more of the following categories: anti-cancer drugs; anti-inflammatory agents; anti-bacterial; anti-fibrotic; and analgesic. The one or more drug compounds or pharmaceutically acceptable salt, solvate or solvate of the salt thereof may be hydrophobic. The one or more drug compounds or pharmaceutically acceptable salt, solvate or solvate of the salt thereof may be hydrophilic.

The anti-cancer drug may be selected from one or more of the following: Actinomycin; All-trans retinoic acid; Azacitidine; Azathioprine; Bleomycin; Bortezomib; Carboplatin; Capecitabine; Cisplatin; Chlorambucil; Cyclophosphamide; Cytarabine; Daunorubicin; Docetaxel; Doxifluridine; Doxorubicin; Epirubicin; Epothilone; Etoposide; Fluorouracil; Gemcitabine; Hydroxyurea; Idarubicin; Imatinib; Irinotecan; Mechlorethamine; Mercaptopurine; Methotrexate; Mitoxantrone; Oxaliplatin; Paclitaxel; Pemetrexed; Teniposide; Tioguanine; Topotecan; Valrubicin; Vemurafenib; Vinblastine; Vincristine; Vindesine; and Vinorelbine.

The anesthetic drug may be a local anesthetic selected from one or more of the following: Procaine; Benzocaine; Chloroprocaine; Cocaine; Cyclomethycaine; Dimethocaine/ Larocaine; Piperocaine; Propoxycaine; Procaine/Novocaine; Proparacaine; Tetracaine/Amethocaine; Articaine; Bupivacaine; Cinchocaine/Dibucaine; Etidocaine; Levobupivacaine; Lidocaine/Lignocaine/Xylocaine; Mepivacaine; Prilocaine; Ropivacaine; and Trimecaine. The anesthetic drug may be a local anesthetic selected from one or more of the following: Procaine; Benzocaine; Chloroprocaine; Cyclomethycaine; Dimethocaine; Piperocaine; Propoxycaine; Procaine; Proparacaine; Tetracaine; Articaine; Bupivacaine; Cinchocaine; Etidocaine; Levobupivacaine; Lidocaine; Mepivacaine; Prilocaine; Ropivacaine; and Trimecaine. The anesthetic drug may be Lidocaine.

BRIEF DESCRIPTION OF THE DRAWINGS

FIG. 8 shows the release of docetaxel (1%), bicalutamide (4%), and VPC-27 (4%) from PEG:PLGA polymeric pastes (50:50 (A) or 55:45 (B) or 60:40 (C)).

DETAILED DESCRIPTION OF THE INVENTION

Figure 1:
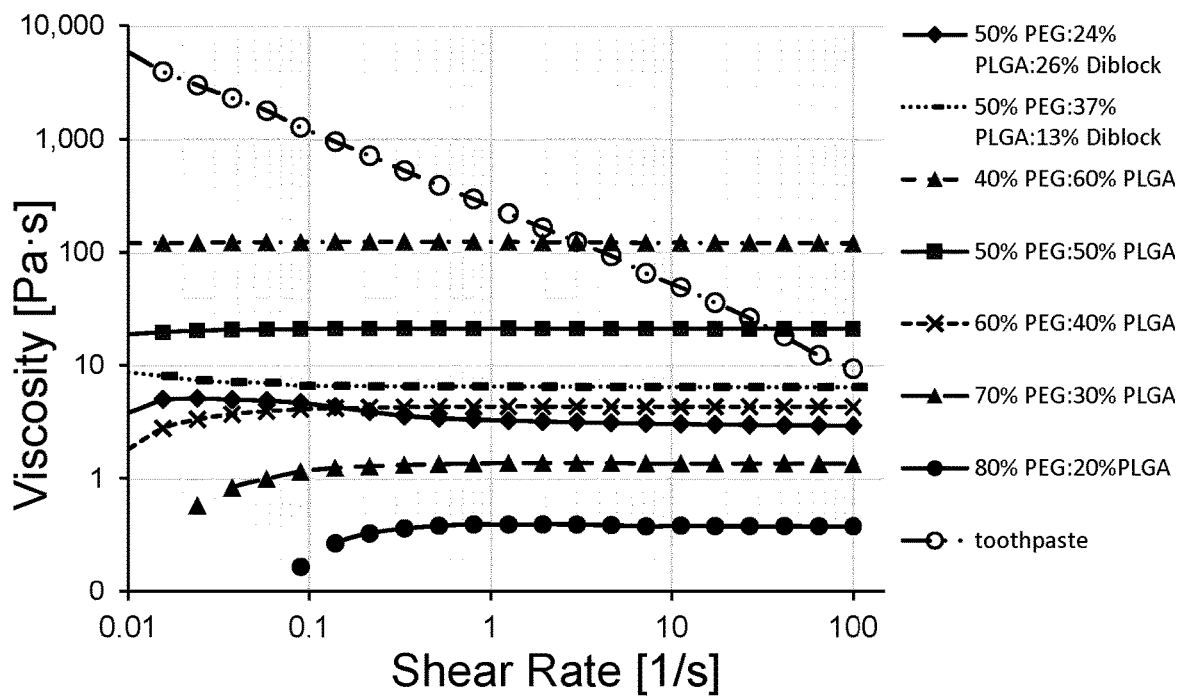
FIG. 1 shows the viscosity of polymeric pastes with different weight ratios of PLGA, PEG and diblock copolymer.

In embodiments of the invention hydrophobic water-insoluble polymers are used to control the consistency of biocompatible polymer pastes and subsequent release of a variety of drugs therefrom.

Inherent Viscosity (IV) is a viscometric method for measuring molecular size. IV is based on the flow time of a polymer solution through a narrow capillary relative to the flow time of the pure solvent through the capillary. The units of IV are typically reported in deciliters per gram (dL/g). IV is simple and inexpensive to obtain and reproducible. Gel Permeation Chromatography (GPC) may be used as a chromatographic method for measuring molecular size. The molecular size can be expressed as molecular weight (MW) in Daltons obtained from calibration with a standard polymer (for example, polystyrene standards in chloroform). The molecular weight of styrene is 104 Daltons and standards of known polystyrene are readily available. MWs obtained by GPC are very method-dependent and are less reproducible between laboratories. Alternatively, molecular weight may be measured by size exclusion chromatography (SEC), high temperature gel permeation chromatography (HT-GPC) or mass spectrometry (MALDI TOF-MS).

The hydrophobic water-insoluble polymers may be a polyester. The hydrophobic water-insoluble polymers may be a polylactic-co-glycolic acid (PLGA), wherein, the ratio of LA:GA is equal to or below 75:25. The ratio of LA:GA may be about 50:50. Durect Corporation™ who supplied the PLGA used in these experiments graph inherent viscosity (IV) in dL/g in hexafluoroisopropanol (HFIP) against molecular weight in Daltons for their 50:50 and 65:35 LA:GA polymers. Similarly, when Durect™ calculated the IV values in dL/g for 75:25 PLGA and 85:15 PLGA, chloroform, was used as the solvent. The relationship between IV and molecular weight in Daltons is different depending on the ratio of LA:GA. As described herein an inherent viscocity of between 0.15 to 0.25 dL/g is an optional range, but an IV in the range 0.25-0.5 dL/g would also be suitable. Alternatively, the range may be between about 0.15 dL/g and about 0.5 dL/g.

Using a 50:50 PLGA a range of 0.15 to 0.25 dL/g is approximately equivalent to a range of about 4,300 Daltons to about 6,700 Daltons and of 0.25 to 0.5 dL/g is approximately equivalent to a range of about 6,700 Daltons to about 26,600 Daltons. Using a 65:35 PLGA a range of 0.15 to 0.25 dL/g is approximately equivalent to a range of about 6,500 Daltons to about 14,200 Daltons and a range of 0.25 to 0.5 dL/g is approximately equivalent to a range of about 14,200 Daltons to about 39,000 Daltons. The broader range of 0.15 to 0.5 dL/g is equivalent to about 4,300 Daltons to about 26,600 daltons for 50:50 PLGA and about 6,500 Daltons to about 39,000 daltons for 65:35 PLGA. Accordingly, the Dalton range for PLGA may be anywhere between 4,300 and about 39,000. Alternatively, the Dalton range for PLGA may be anywhere between 4,300 and about 40,000 or higher if using 75:25 (i.e. up to a molecular weight of 56,500 Dalton). For the 50:50, 65:35 and 75:25 LA:GA polymers, an IV of 0.5 g/dL approximately corresponds to molecular weights of 26,600, 39,000, and 56,500. As tested the Durect™ 50:50 having an IV of 0.25 dL/g is about 6,700 Daltons, Durect™ 75:25 having an IV of 0.47 dL/g is about 55,000 Daltons and Durect™ 85:15 having an IV of 0.55 dL/g to 0.75 dL/g is in the range of about 76,000 Daltons to about 117,000 Daltons.

Calculations of IV to Dalton's provided by Durect Corporation™ are as follows (for each ratio of LA:GA). For 50:50 an IV of 0.25 dL/g is about 6.700 Daltons, an IV of 0.35 dL/g is about 12,900, Daltons, an IV of 0.45 dL/g is about 21,100, an IV of 0.55 dL/g is about 31,100 Daltons and an IV of 0.65 dL/g is about 43.500 Daltons. For 65:35 an IV of 0.15 dL/g is about 6,500 Daltons, an IV of 0.25 dL/g is about 14,200 Daltons, an IV of 0.35 dL/g is about 23,700 Daltons, an IV of 0.45 dL/g is about 34,600 Daltons, an IV of 0.55 dL/g is about 47,000 Daltons and an IV of 0.65 dL/g is about 60,500 Daltons. For 75:25 an IV of 0.15 dL/g is about 11,200 Daltons, an IV of 0.25/0.3 dL/g is about 23,800 Daltons, an IV of 0.35/0.4 dL/g is about 39,000 Daltons, an IV of 0.45/0.5 dL/g is about 56,500 Daltons and an IV of 0.55/0.6 dL/g is about 76,000 Daltons.

Of particular interest are PLGA pastes having a ratio of LA:GA of 50:50 with an IV of between 0.15 dL/g to 0.25 dL/g (i.e. molecular weights of between 4,300 Daltons to 6,700 Daltons). However, PLGA pastes having a ratio of LA:GA of 50:50 with an IV of 0.25 dL/g to 0.5 dL/g (i.e. a molecular weight of about 6,700 to about 26,600 Daltons) is also useful.

The PLGA polymer molecular weight may be reported as inherent viscocity (IV)) may be IV=0.15-0.5 dL/g. The PLGA polymer IV may be <0.3 dL/g. The PLGA polymer density may lie between 0.15-0.25 dL/g. Low molecular weight versions of PLGA with a 50:50 ratio of LA:GA and an inherent viscosity under 0.3 dL/g may be rendered fully miscible with a low molecular weight biocompatible glycol using mild heating to form either a viscous or fluid paste at room temperature. For high viscosity pastes, the 50:50 ratio PLGA materials with an inherent viscosity up to 0.5 dL/g may be used with poly ethylene glycol (PEG). PEG or mePEG with a molecular weight below 1450 may be used in these applications. The low molecular weight biocompatible glycol may have a molecular weight between about 76 and about 1450. The PEG or mePEG may have an average molecular weight of between 300 and 1450.

Low molecular weight biocompatible glycol may be used to fluidize PLGA to a paste and set to an implant. Examples of a low molecular weight biocompatible glycol may include PEG, mePEG and propylene glycol. A PEG-based glycol (i.e. mePEG or PEG) may have a molecular weight of up to 1450. Alternatively, the PEG-based excipient may have a molecular weight 900. In a further alternative, a PEG-based excipient may have a molecular weight of about 300. PEG 300™ is biocompatible and is directly cleared via the kidneys without liver or other degradation required.

PLGA:PEG pastes may be loaded with a variety of drugs and allow for controlled release of the loaded drug(s) over periods of approximately 1-2 months. Low molecular weight diblock copolymers may also be optionally incorporated without phase separation into the PLGA:PEG compositions with only minor changes in viscosity of the total composition. The presence of diblock copolymers may allow further control (acceleration) of drug release from the polymer matrix so that certain drugs that release slowly may be released more rapidly.

Diblock copolymers may consist of two different types of monomers. The monomers may be hydrophobic. The monomers may be hydrophilic. The diblock copolymer may have one hydrophobic monomer and one hydrophilic monomer. The diblock copolymer may be amphiphilic. The hydrophilic monomer for example, may be PEG or MePEG. The hydrophobic monomer for example, may be PLGA, PLA, PLLA or PCL. TABLE 1 below provides a range of compositions that were made and tested to determine their characteristics and useful features.

TABLE 1 provides examples of various polymer formulations as tested.

| PLGA IV or alternative | % Glycol | Optional Diblock % Copolymer | | Form at % injection | Injectability (needle size/force) | Set time in water starts |
|---|---|---|---|---|---|---|
| 0.15-0.25 | 25 PEG 300 ™ | 75 | | Fluid paste | 23 gauge/easy | 1 minute |
| 0.15-0.25 | 37 PEG 300 ™ | 63 | | paste | 22 gauge/easy | 1 minute |
| 0.15-0.25 | 50 PEG 300 ™ | 50 | | paste | 22 gauge/moderate | 1 minute |
| 0.15-0.25 | 24 PEG 300 ™ | 50 Diblock | 26 | paste | 22 gauge/moderate | 1-2 minutes |
| 0.15-0.25 | 37 PEG 300 ™ | 50 Diblock | 13 | paste | 22 gauge/easy-moderate | 1-2 minutes |
| 0.15-0.25 | 40 PEG 750 ™ | 60 | | paste | 22 gauge/moderate | 1-2 minutes |
| 0.15-0.25 | 40 PEG 900 ™ | 60 | | paste | 22 gauge/difficult | 3-5 minutes |
| 0.15-0.25 | 30 PEG 1450 ™ | 70 | | Wax/paste | 16 gauge/difficult/ needs 37° C. | 1 minute |

-continued

| PLGA IV or alternative | % Glycol | | Optional Diblock % Copolymer | | Form at injection | Injectability (needle size/force) | Set time in water starts |
|---|---|---|---|---|---|---|---|
| 0.15-0.25 | 40 | MethoxyPEG 750 | 60 | | paste | 22 gauge/ moderate | 1-2 minutes |
| 0.15-0.25 | 50 | Propylene Glycol | 50 | | Very viscous paste | 16 gauge/difficult | 1 hour |
| 0.25-0.50 | 35 | PEG 300 ™ | 65 | | Medium viscous paste | 18 gauge/e 16 gauge/easy | 5 minutes |
| 0.47-0.55* | 50 | PEG 300 ™ | 50 | | Very viscous paste | 16 gauge/difficult | 1 hour |
| 0.47-0.55* | 40 | PEG 300 ™ | 60 | | viscous paste | 16 gauge easy | 0.5-1 hour |
| 0.47-0.55* | 30 | PEG 300 ™ | 70 | | paste | 16 gauge easy | 3-5 min |
| 0.47-0.55* | 20 | PEG 300 ™ | 80 | | liquid paste | 16 gauge/very easy | 1 minute, but dissolves away |
| More viscous injectables (needs pressure for injection - waxy prior to injection, delayed set time) | | | | | | | |
| 0.25-0.50 | 35 | Propylene glycol | 65 | | Almost solid/paste | 16 gauge/extreme force | 1-2 hour |
| 0.15-0.25 | 50 | Pluronic L101 ™ | 50 | | Very viscous paste | 16 gauge/difficult | 1 hour |
| PLLA 2K | 40 | PEG 300 ™ | 60 | | Wax | 16 gauge/extreme | 5 minutes |
| PCLdiol 1250 | 60 | PEG 300 ™ | 40 | | Wax | 18 gauge/difficult | 2 minutes sets to v hard implant |
| Not injectable using normal gauge needles or a reasonable amount of force | | | | | | | |
| 0.55-0.75 | 20 | PEG 300 ™ | 80 | | No homogenous paste | Not injectable | n/a |
| 0.55-0.75 | 30 | PEG 300 ™ | 70 | | No homogenous paste | Not injectable | n/a |
| 0.55-0.75 | 40 | PEG 300 ™ | 60 | | No homogenous paste | Not injectable | n/a |
| 0.55-0.75 | 50 | PEG 300 ™ | 50 | | No homogenous paste | Not injectable | n/a |

*the PLGA was not from Durect ™ and the IV values for these PLGAs were estimated based on the ratio of LA:GA of 75:25.

Drug delivery compositions described herein may exist in a variety of "paste" forms. Examples of paste forms may include liquid paste, paste or wax-like paste, depending on to polymers used, the amount of the polymers used and the temperature.

Drug delivery compositions described herein may release one or more drugs over a period of several hours or over several months, depending on the need. Compositions described herein may be used for localized delivery of one or more drugs to a subject. Examples of drugs that may be delivered using these compositions are not limited, and may include anti-cancer drugs, anti-inflammatory agents, anti-bacterial, anti-fibrotic, analgesic. Examples of anti-cancer drugs that may be used with the compositions of the present invention include docetaxel, paclitaxel, mitomycin, cisplatin, etoposide vinca drugs, doxorubicin drugs, rapamycin, camptothecins, gemcitabine, finasteride (or other cytotoxics); bicalutamide, enzalutamide, VPC-27, tamoxifen, sunitinib, erlotinib. Anti-cancer biological agents may also be used in the formulation such as antibody based therapies e.g. Herceptin, Avastin, Erbitux or radiolabelled antibodies or targeted radiotherapies such as PSMA-radioligands. Anti-inflammatory agents may include non-steroidal drugs like ibuprofen, steroids like prednisone. Local analgesia or local anesthetic medications may include, for example, one or more of the following: Procaine; Benzocaine; Chloroprocaine; Cocaine; Cyclomethycaine; Dimethocaine/Larocaine; Piperocaine; Propoxycaine; Procaine/Novocaine; Proparacaine; Tetracaine/Amethocaine, Articaine; Bupivacaine; Cinchocaine/Dibucaine; Etidocaine; Levobupivacaine; Lidocaine/Lignocaine/Xylocaine; Mepivacaine; Prilocaine; Ropivacaine; and Trimecaine. Antibiotic medications may include penicillin, cephalexin, gentamicin, ciprofloxacin, clindamycin, macrodantin, and others. The drugs may be hydrophobic or may be hydrophilic. Specific drugs may be selected from one of more of the following: Docetaxel; VPC-27; Bicalutamide; Cephalexin (A); Sunitinib; Tamsulosin; Desoximetasone; Gemcitabine; Rapamycin; and Ibuprofen.

Hydrophobic drugs may be able to bind with strong affinity to the hydrophobic water-insoluble polymer (ex. PLGA) allowing slow dissociation and controlled release from the implant. Such drugs tend to dissolve (at least partially) in the paste mixture. Hydrophilic drugs may be blended into the paste but because the matrix is partially hydrated in aqueous environments, these drugs may dissolve out of the implant quickly. In some situations this may be desirable, such as when an antibacterial drug may be included in the paste to treat a local infection and it is preferred if all the drug is cleared form the paste in 7 days to suit an antibacterial drug treatment regime.

Drug delivery compositions may be prepared and utilized to treat or prevent a variety of diseases or conditions. Examples of diseases or conditions that may be treated, may for example, include cancer, pain, inflammatory conditions, fibrotic conditions, benign tumors (including benign prostate hyperplasia), and infections.

Local anesthetics usually fall into one of two classes: aminoamide and aminoester. Most local anesthetics have the suffix "-caine". The local anesthetics in the aminoester group may be selected from one or more of the following: Procaine; Benzocaine; Chloroprocaine; Cocaine; Cyclomethycaine; Dimethocaine/Larocaine; Piperocaine; Propoxycaine; Procaine/Novocaine; Proparacaine and Tetracaine/Amethocaine. The local anesthetics in the aminoamide group may be selected from one or more of the following: Articaine; Bupivacaine; Cinchocaine/Dibucaine; Etidocaine; Levobupivacaine; Lidocaine/Lignocaine/Xylocaine; Mepivacaine; Prilocaine; Ropivacaine; and Trimecaine. Local anesthetics may also be combined (for example, Lidocaine/prilocaine or Lidocaine/tetracaine).

Furthermore, local anesthetics used for injection may be mixed with vasoconstrictors to increase residence time, and the maximum doses of local anesthetics may be higher when used in combination with a vasoconstrictor (for example, prilocaine hydrochloride and epinephrine; lidocaine, bupivacaine, and epinephrine; lidocaine and epinephrine; or articaine and epinephrine).

Anti-cancer drugs as may be used in the composition described herein, may be categorized as alkylating agents (bi and mono-functional), anthracyclines, cytoskeletal disruptors, epothilone, topoisomerase inhibitors (I and II), kinase inhibitors, nucleotide analogs and precursor analogs, peptide antibiotics, platinum-based agents, vinka alkaloids, and retinoids. Alkylating agents, may be bifunctional alkylators (for example, Cyclophosphamide, Mechlorethamine, Chlorambucil and Melphalan) or monofunctional alkylators (for example, Dacarbazine (DTIC), Nitrosoureas and Temozolomide). Examples of anthracyclines are Daunorubicin, Doxorubicin, Epirubicin, Idarubicin, Mitoxantrone, and Valrubicin. Cytoskeletal disruptors or taxanes are Paclitaxel, Docetaxel, Abraxane and Taxotere. Epothilones may be epothilone or related analogs. Histone deacetylase inhibitors may be Vorinostat or Romidepsin. Inhibitors of topoisomerase I may include Irinotecan and Topotecan. Inhibitors of topoisomerase II may include Etoposide, Teniposide or Tafluposide. Kinase inhibitors may be selected from Bortezomib, Erlotinib, Gefitinib, Imatinib, Vemurafenib or Vismodegib. Nucleotide analogs and precursor analogs may be selected from Azacitidine, Azathioprine, Capecitabine, Cytarabine, Doxifluridine, Fluorouracil, Gemcitabine, Hydroxyurea, Mercaptopurine, Methotrexate or Tioguanine/Thioguanine. Peptide antibiotics like Bleomycin or Actinomycin. Platinum-based agents may be selected from Carboplatin, Cisplatin or Oxaliplatin. Retinoids may be Tretinoin, Alitretinoin or Bexarotene. The Vinca alkaloids and derivatives may be selected from Vinblastine, Vincristine, Vindesine and Vinorelbine.

An anti-cancer drug that may be used with the compositions described herein, may be selected from one or more of: Actinomycin; All-trans retinoic acid; Azacitidine; Azathioprine; Bleomycin; Bortezomib; Carboplatin; Capecitabine; Cisplatin; Chlorambucil; Cyclophosphamide; Cytarabine; Daunorubicin; Docetaxel; Doxifluridine; Doxorubicin; Epirubicin; Epothilone; Etoposide; Fluorouracil; Gemcitabine; Hydroxyurea; Idarubicin; Imatinib; Irinotecan; Mechlorethamine; Mercaptopurine; Methotrexate; Mitoxantrone; Oxaliplatin; Paclitaxel; Pemetrexed; Teniposide; Tioguanine; Topotecan; Valrubicin; Vemurafenib; Vinblastine; Vincristine; Vindesine; and Vinorelbine. Alternatively, the anti-cancer drug may be a biological agent and may be selected from Herceptin (Trastuzumab), Ado-trastuzumab, Lapatinib, Neratinib, Pertuzumab, Avastin, Erbitux or radio-labelled antibodies or targeted radiotherapies such as PSMA-radioligands. The anti-cancer drug may be an Androgen Receptor, an Estrogen Receptor, epidermal growth factor receptor (EGFR) antagonists, or tyrosine kinase inhibitor (TKI). An anti-angiogenesis agent may be selected from avastin, an epidermal growth factor receptor (EGFR) antagonists or tyrosine kinase inhibitor (TKI). An Immune modulator such as Bacillus Calmette-Guerin (BCG).

As used herein a "drug" refers to any therapeutic moiety, which includes small molecules and biological agents (for example, proteins, peptides, nucleic acids). Furthermore, a biological agent is meant to include antibodies and antigens. As used herein, the term drug may in certain embodiments include any therapeutic moiety, or a subset of therapeutic moieties. For example, but not limited to one or more of the potentially overlapping subsets and one or more drugs, as follows: hydrophobic drugs, hydrophilic drugs; a cancer therapeutic drug; a local anesthetic drug; an anti-biotic drug; an anti-viral drug; an anti-inflammatory drug; a pain drug; an anti-fibrotic drug; or any drug that might benefit from a localized and/or sustained release.

As used herein, "an antibody" is a polypeptide belonging to the immunoglobulin superfamily. In particular, "an antibody" includes an immunoglobulin molecule or an immunologically active fragment of an immunoglobulin molecule (i.e., a molecule(s) that contains an antigen binding site), an immunoglobulin heavy chain (alpha ($\alpha$), mu ($\mu$), delta ($\delta$) or epsilon ($\epsilon$)) or a variable domain thereof (VH domain), an immunoglobulin light chain (kappa ($\kappa$) or lambda ($\lambda$)) or a variable domain thereof (VL domain), or a polynucleotide encoding an immunoglobulin molecule or an immunologically active fragment of the immunoglobulin molecule. Antibodies includes a single chain antibody (e.g., an immunoglobulin light chain or an immunoglobulin heavy chain), a single-domain antibody, an antibody variable fragment (Fv), a single-chain variable fragment (scFv), an scFv-zipper, an scFv-Fc, a disulfide-linked Fv (sdFv), a Fab fragment (e.g., CLVL or CHVH), a F(ab') fragment, monoclonal antibodies, polyclonal antibodies. As used herein "antigen" refers to any epitope-binding fragment and a polynucleotide (DNA or RNA) encoding any of the above.

As used herein, a "paste" is any composition described herein that has the characteristics of a solid and of a liquid depending on applied load and the temperature. Specifically, the viscosity of a paste may be anywhere in the range of about 0.1 to about 200 pascal seconds (Pa·s) at room temperature and may be measured by any number of methods known to those of skill in the art. Numerous types of viscometers and rheometers are known in the art. For example, a cone and plate rheometer (i.e. Anton Paar™, MCR 502).

As used herein a "swelling agent" is meant to encompass any biocompatible agent that will increase the volume of a paste as described herein, once the paste with swelling agent incorporated is placed in an aqueous environment. A swelling agent may be selected from: salts of hyaluronic acid (e.g., sodium hyaluronate); cellulose derivatives (e.g., carboxymethylcellulose); or polyacrylic acid derivatives (e.g., Carbomers). A swelling agent may advantageously be approved for use in injectable compositions. Also having a swelling agent that does not interfere with the injectability of the paste (for example, is not too grainy, does not precipitate and is easy to disperse again) would be of benefit. It may also be advantageous, if the swelling agent is able to provide a suitable amount of swelling without reducing the overall % of the polymers of the paste as described herein (i.e. be a small percentage of the overall paste). Furthermore, a swelling agent that exhibits high rate of swelling and quick swelling characteristics (for example, swell within minutes of injection) would be beneficial.

Methods

Paste Preparation

The paste was prepared by weighing the polymers into a glass vial and stirring at 60° C. The polymers formed a homogenous melt. If drug is to be added, it is added following the polymer paste preparation. The values for the paste polymers (i.e. hydrophobic water-insoluble polymer; low molecular weight biocompatible glycol; and, if used, the di-block copolymer and/or swelling) is prepared as a total % out of 100% before mixing with drug. When the drug is added the % associated therewith is a percent of the total composition with drug and the "pre-drug paste" component %s are based on their proportions prior to adding the drug. For example, 4% means 4 g of drug in 100 g paste. Drug(s) were incorporated using levigation or a mortar and pestle.

The injectability of a paste will depend on many parameters (i.e. needle size, needle lengths, volume, tissue back-pressure, strength of the person administering the paste). Normally it is preferred that a paste be easily drawn up into a syringe using a 14 gauge needle and easily injected into a tissue zone using an 18 gauge or even smaller needle with a small amount of extra pressure. However, for particular uses and depending on the gauge of the needle, having a more viscous paste (i.e. more difficult to inject), may be desirable.

Viscosity Measurement

Viscosity measurements were taken using a cone plate rheometer (Anton Paar™, MCR 502) and recorded as a function of shear rate at constant temperature.

Water Absorption by Pastes Containing a Swelling Agent

Pastes containing a swelling agent were prepared by incorporating increasing amounts of a base paste (PEG: PLGA) into the swelling agent (sodium hyaluronate) using mortar and pestle. Around 20 mg of paste samples (n=3) for each paste formulation were weighed on filter membranes (0.45 µm) and repeatedly weighed after soaking in water at 37° C. For each time point, excess water was carefully removed using a vacuum pump.

In Vitro Drug Release Assays

The drug-loaded paste can be aliquoted for in vitro release studies. Paste (50-100 mg) is deposited at the bottom of a test tube and release medium is added (5-10 mL, sink conditions). Release medium is phosphate buffered saline (PBS, 10 mM, pH 7.4)) or PBS containing 1% Albumin. The test tubes are kept in a 37° C. incubator until the end of the study. Release samples are taken at appropriate time points by replacing the complete release medium (supernatant) and analyzing it for total drug using Reversed phase high-performance liquid chromatography with ultraviolet (UV) detection (RP-HPLC-UV).

TABLE 1

Chromatographic parameters used in RP-HPLC

| Parameter | Specification |
| --- | --- |
| HPLC | Waters (1525 Binary HPLC Pump, 2489 UV/Visible Detector, 717 plus Autosampler) |
| Detector | UV/Visible |
| Flow rate | 1 mL/min |
| Column | C-18, Nova-Pak, 4 µm, 3.9 × 150 mm |
| Column Temperature | Ambient, no temperature control |
| Injection Volume | 20 µL |
| Elution | isocratic |

TABLE 2

Mobile phase, retention times and UV detection wavelength for studied drugs.

| Drug | Mobile phase composition (v/v) | Retention time (min) | UV detection wavelength (nm) |
| --- | --- | --- | --- |
| Bicalutamide/enzalutamide | 30/30/40 Acetonitrile/methanol/water (adjusted to pH 3.4 with glacial acetic acid) | 3 min | 272 |
| Docetaxel | 30/30/40 Acetonitrile/methanol/water (adjusted to pH 3.4 with glacial acetic acid) | 6 min | 228 |
| VPC-27 | 300/180/35 Acetonitrile/methanol/water + 200 µL glacial acetic acid | 4.3 min | 244 |
| Rapamycin | 200/175/125 Acetonitrile/methanol/water | 2.9 min | 278 |
| Cephalexin | 20/80 Acetonitrile/water (adjusted to pH 3.4 with glacial acetic acid) | 5 min | 254 |
| Lidocaine | 50/50 Acetonitrile/ammoniumacetate 20 mM (pH 6.4) | 3.2 min | 220 |
| Desoximetasone | 50/50 Acetonitrile/ammoniumacetate 20 mM (pH 6.4) | 2 min | 244 |
| Sunitinib | 55/45 Acetonitrile/ammoniumacetate 20 mM (pH 6.4) | 4 min | 431 |

TABLE 2-continued

Mobile phase, retention times and UV detection wavelength for studied drugs.

| Drug | Mobile phase composition (v/v) | Retention time (min) | UV detection wavelength (nm) |
|---|---|---|---|
| Tamsulosin | 50/50 Acetonitrile/ammoniumacetate 20 mM (pH 6.4) | 2.3 min | 220 |
| Ibuprofen | 50/50 Acetonitrile/ammoniumacetate 20 mM (pH 6.4) | 1.9 min | 220 |
| Gemcitabine | 3/97 methanol/water (adjusted to pH 3.4 with glacial acetic acid) | 2.3 min | 272 |

Intratumoral Paste Injection

Athymic male nu/nu mice (uncastrated) have been injected with 4×10⁶ LNCap cells suspended in Matrigel™ subcutaneously in the left flank. Treatment allocation began once a single site tumor reached 150-200 mm³ via caliper measurement. Drug-loaded paste (30 µL) was injected into the tumor using a 21 gauge needle. Serum prostate specific antigen (PSA) levels were measured over time and tumor size was monitored.

In another experiment, groups of five to six animals received 30-40 µL paste intratumorally once the tumor had reached a size of 100 mm³. Tumor growth and serum PSA levels were monitored for the following 12 weeks. Local delivery of paste subcutaneously in rats.

Five groups of rats (male, Sprague Dawley™) with six animals in each group received one injection of paste formulation (0.1 mL) subcutaneously in their flank. The paste formulation was based on a 50:50 mixture of PEG 300™ and PLGA. Lidocaine was incorporated into the paste at 80, 100, 120, 140, and 160 mg per g of paste. The corresponding doses for each group were 23, 29, 36, 40 and 45 mg of Lidocaine per kg.

Blood was collected from the saphenous vein over four weeks at 0, 0.25, 1, 4, 24, 48, 168 336, 504 and 672 hours after injection. Lidocaine concentrations in rat serum were determined using ultra high performance liquid chromatography tandem mass spectrometry (UHPLC-MS/MS). A non-compartmental analysis was then applied to each data set using Phoenix 64™ (Build 6.3.0.395) WinNonlin 63™ to determine relevant pharmacokinetic parameters.

Kidney Pelvis Injection of Paste

After placement of a ureteral catheter, three pigs received an injection of 1-2 mL of polymeric paste into the kidney pelvis. After removal of the ureteral catheter, a urinary catheter was placed and urine collected for 3 h intervals over 24 h. Blood was collected from an ear vein over 24 h and gemcitabine concentrations were determined using ultra high performance liquid chromatography tandem mass spectrometry (UHPLC-MS/MS).

EXAMPLES

Example 1

Viscosity of Polymeric Pastes Manufactured Using Different Ratios of PLGA, PEG and Diblock Copolymer The polymeric paste is a biocompatible formulation comprised of two or three constituents: poly-(lactic-co-glycolic) acid (PLGA), a diblock copolymer of DL-lactide (DLLA) (optional) and methoxy polyethylene glycol (mePEG) termed poly(DL-lactide)-methoxy polyethylene glycol (PDLLA-mePEG), and polyethylene glycol with a molecular weight of 300 Da (PEG 300™). Drug or drug mixtures can be incorporated into the paste through levigation with a spatula and the paste can be injected through a 20 G needle. The PLGA is comprised of equal amounts of LA and GA (50:50 Poly[DL-lactide-co-glycolide]) and may have a degradation time of 1-2 months. The polymeric drug delivery paste may be an injectable viscous solution at 37° C. After injection into an aqueous tissue environment, the paste may transform into a waxy solid, which may serve as a sustained release platform for incorporated drug(s).

Polymeric pastes were manufactured using different weight ratios of PLGA (Durect™, Alabama) (IV=0.15-0.25 dL/g, 50:50 ratio of LA to GA), PEG with a molecular weight of 300 Da (Polysciences™, USA) and diblock copolymer (synthesized in house, MW=3333 Da, comprising 40% PLLA and 60% methoxypolyethylene glycol (w:w)). The diblock copolymer may be used to adjust the degradation profile of the polymeric paste and the release profile of the drug(s). The diblock copolymer can help to encapsulate hydrophobic drugs due to its amphiphilic characteristics. In aqueous solution, the diblock can spontaneously arrange itself in micelles that can host hydrophobic drug in the poly (DL lactic acid) (PDLLA) core surrounded by the hydrophilic PEG or mePEG chains[53-55].

The components were weighed into a glass vial and stirred overnight at 37° C. to form a homogenous mixture. Viscosity measurements were taken using a cone plate rheometer (Anton Paar™, MCR 502) and recorded as a shear rate at constant temperature. Pastes comprised of PEG and PLGA had very low viscosities at low PLGA content such that the viscosity of pastes at 80% PEG were less than 1 Pa·s. FIG. 1 shows that as the concentration of PLGA increased, paste viscosity rose very quickly to over 100 Pa s for the 40% PEG and 60% PLGA composition. FIG. 1 also shows that the addition of diblock copolymer in place of PLGA reduced the viscosity considerably so that at 13% diblock with 50% PEG and 37% PLGA the viscosity was less than 10 Pas, and was reduced even further using 26% diblock.

Example 2

The Release of PEG 300™ from Polymeric Paste

Figure 2:
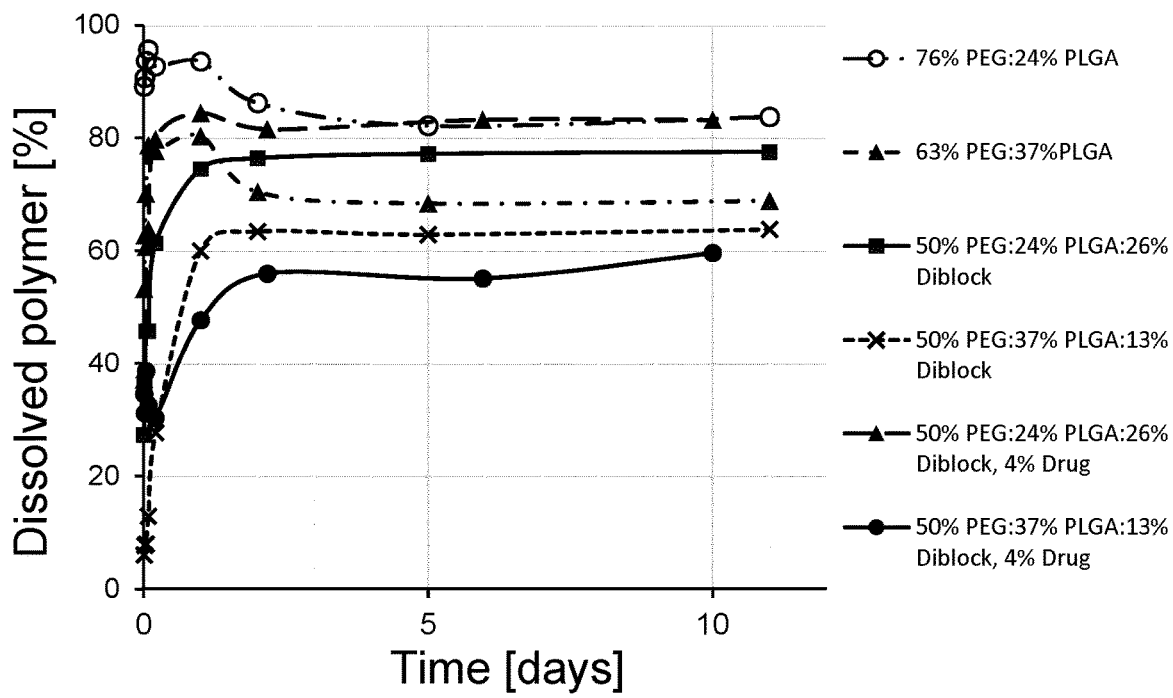
FIG. 2 shows the release of PEG 300™ from several polymeric paste mixtures.

Seven compositions of polymeric pastes were manufactured from PLGA, PEG and diblock copolymer as described in EXAMPLE 1. For each of the seven different polymeric pastes, 8×100 mg each were weighed into the corner of 8×20 ml pre-weighed scintillation vials by holding each vial at a slight angle. 10 ml of water was added to each vial with the vial still held at an angle so the paste remained in the vial corner whilst exposed to water. After 10 minutes the outer surface of each paste whitened slightly indicating setting of the paste and the vials were then reoriented to the vertical position. This procedure prevented a premature disruption of the setting paste upon exposure to water turbulences. The vials were capped and placed in a 37° C. oven. At various time points the vials were removed, water was aspirated and the contents dried for one hour in a 37° C. incubator followed by one day of vacuum drying at room temperature. The vials were then re-weighed to determine the weight loss of water-soluble polymer (PEG or diblock) that dissolved into the water from the polymer paste. FIG. 2 shows that most of the PEG or diblock was released by 2 days.

The values of % polymer released approximately matched the initial weight of PEG and diblock present by % in each formulation.

Example 3

Release of Docetaxel, VPC-27 and Bicalutamide from Polymeric Pastes

Polymeric pastes were manufactured from 50:50, 55:45, 60:40 weight ratio compositions of PLGA (50:50 IV=0.15-0.25 dL/g) and PEG 300™, 50:37:13 ratios of PEG:PLGA:Diblock, or 50:24:26 ratios of PEG:PLGA:Diblock using the methods described in Example 1. The presence of the diblock copolymer allows more detailed control of drug release. This diblock copolymer has been previously described to increase the water solubility of hydrophobic drugs by forming diblock micelles with hydrophobic cores that allows the drugs to partition into the core and increase the apparent solubility. In the paste application as water enters the paste matrix the water soluble diblock begins to dissolve out and any drug dispersed at the molecular level may become "micellized" in the diblock milieu to increase drug release. The drugs VPC-27, bicalutamide or docetaxel were added at various weight ratios directly into the paste with mixing by standard spatula levigation techniques. The drug release was studied according to the descriptions found in the general methods section (In vitro drug release assays, TABLE 1 and TABLE 2).

Figure 3A:
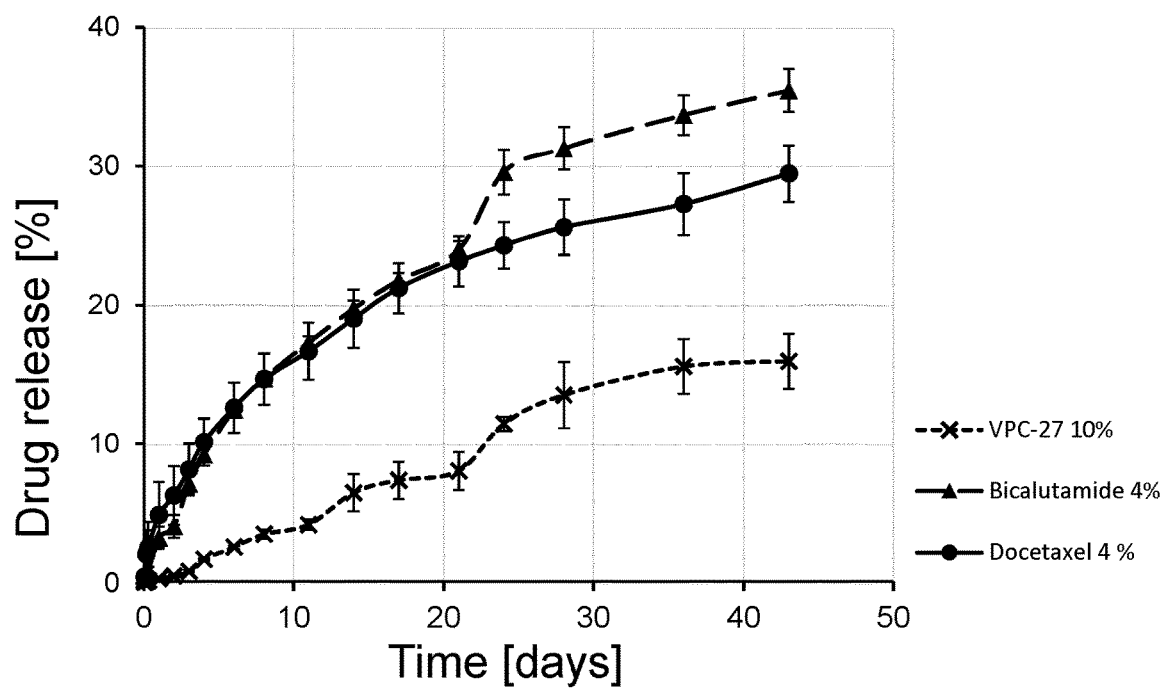
FIG. 3 shows the release of docetaxel at 4%, bicalutamide at 4%, and VPC-27 at 10% (A) and 4% (B) from PEG:PLGA (50:50) polymeric pastes.
Figure 3B:
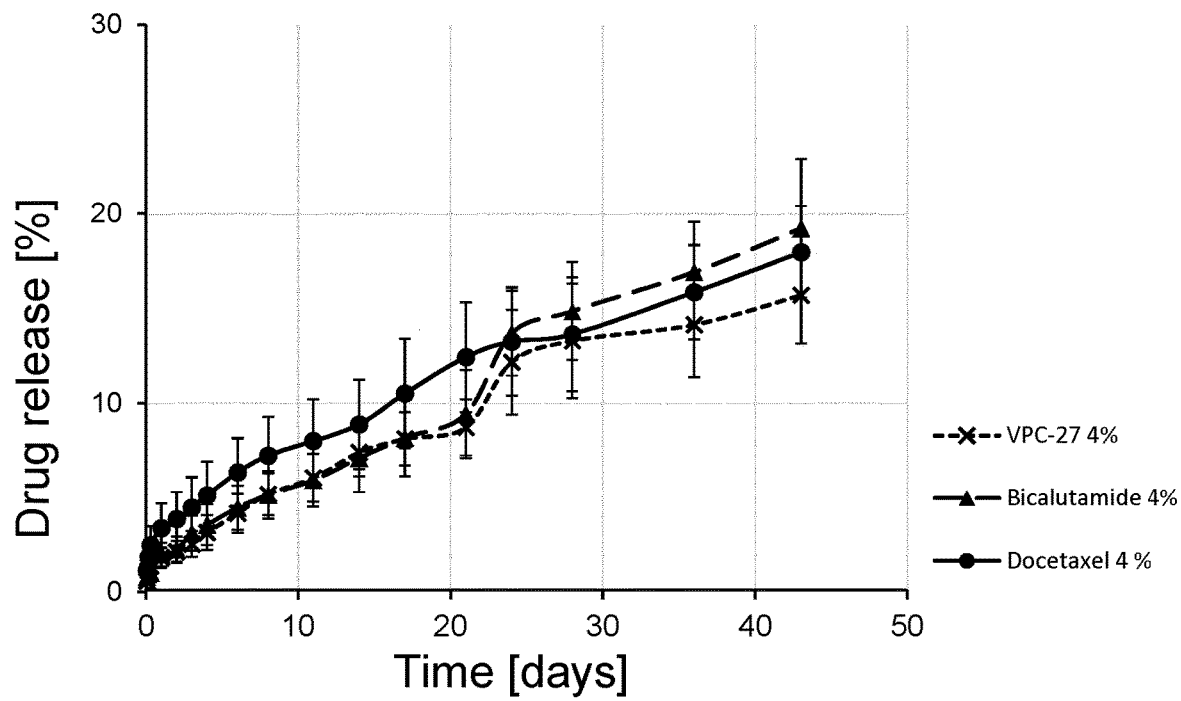

FIG. 3 shows the release of VPC-27, docetaxel and bicalutamide from a 50:50 (PEG:PLGA) paste. Docetaxel (at 4% w/w) and bicalutamide (at 4% w/w) released with similar profiles showing a fast burst of release over 5 days (10% drug released) followed by a slower more sustained release over the next 40 days where a further 20% of encapsulated drug was released (FIG. 3A). VPC-27 (at 10% w/w) released slowly from the paste reaching about 15% of total encapsulated drug released by day 45 (FIG. 3A). When the concentration of VPC-27 was reduced to 4%, the release profiles of docetaxel and bicalutamide were similar to each other but a little slower overall than from the paste containing 10% VPC-27. However, the release rate of VPC-27 was almost the same as the other two drugs using a 4% w/w drug loading (FIG. 36).

Figure 4A:
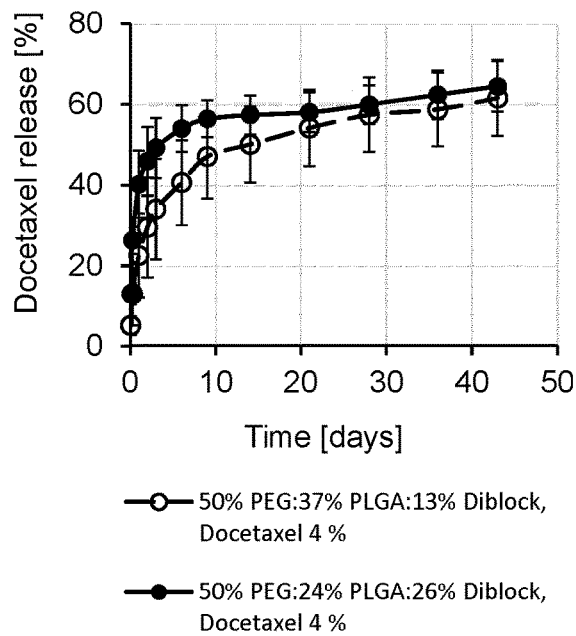
FIG. 4 shows the release of docetaxel (A), bicalutamide (B), and VPC-27 (C) from PEG:PLGA:Diblock polymeric pastes (57:37:13 or 50:24:26).
Figure 4B:
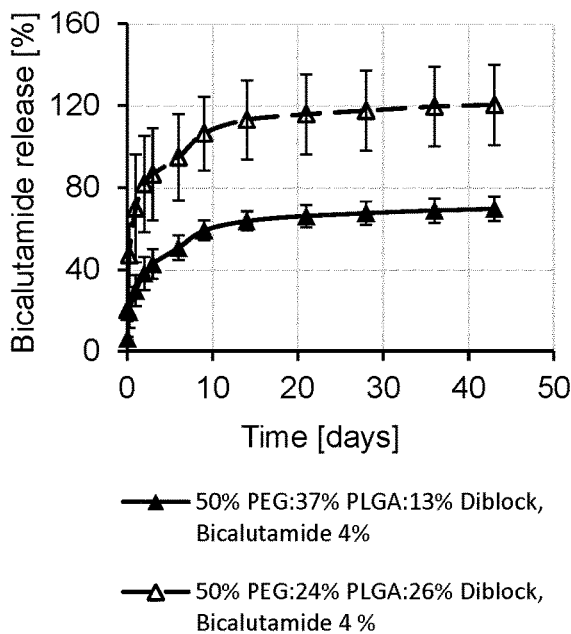
Figure 4C:
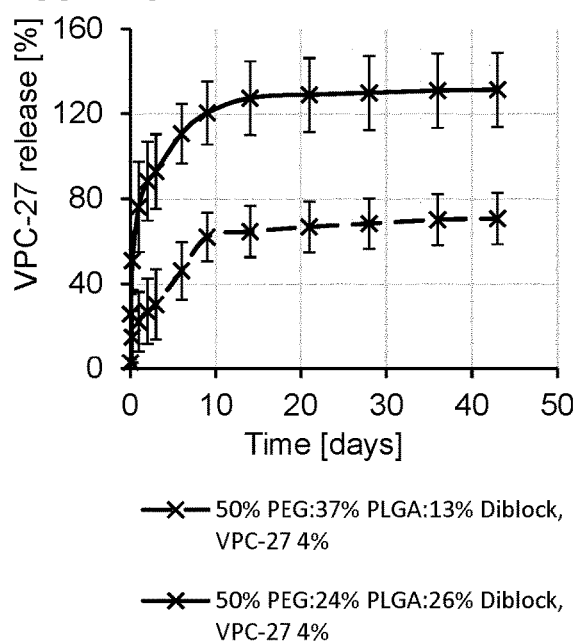

FIG. 4 shows the release of docetaxel, Bicalutamide, and VPC-27 from PEG:PLGA:Diblock pastes 50:37:13 w/w % or 50:24:26 w/w %. FIG. 4A shows that the release rate of docetaxel from 13% and 26% diblock loaded pastes is increased in comparison to the 50:50 paste mixtures shown in FIG. 3 (no diblock). FIG. 4A further shows that by day 10, between 40 and 60% of encapsulated docetaxel was released from the 13% and 26% diblock pastes as compared to less than 17% being released from the 50:50 pastes shown in FIG. 3. The addition of diblock copolymer to the PEG:PLGA paste had a similar effect on the release rates of bicalutamide (FIG. 4B) and VPC-27 (FIG. 4C). By day 10, the release was approximately 60% for both drugs at a diblock loading of 13%, and approximately 100% for pastes containing 26% diblock compared to less than 17% release for either drug from 50:50 pastes with no diblock.

Figure 5:
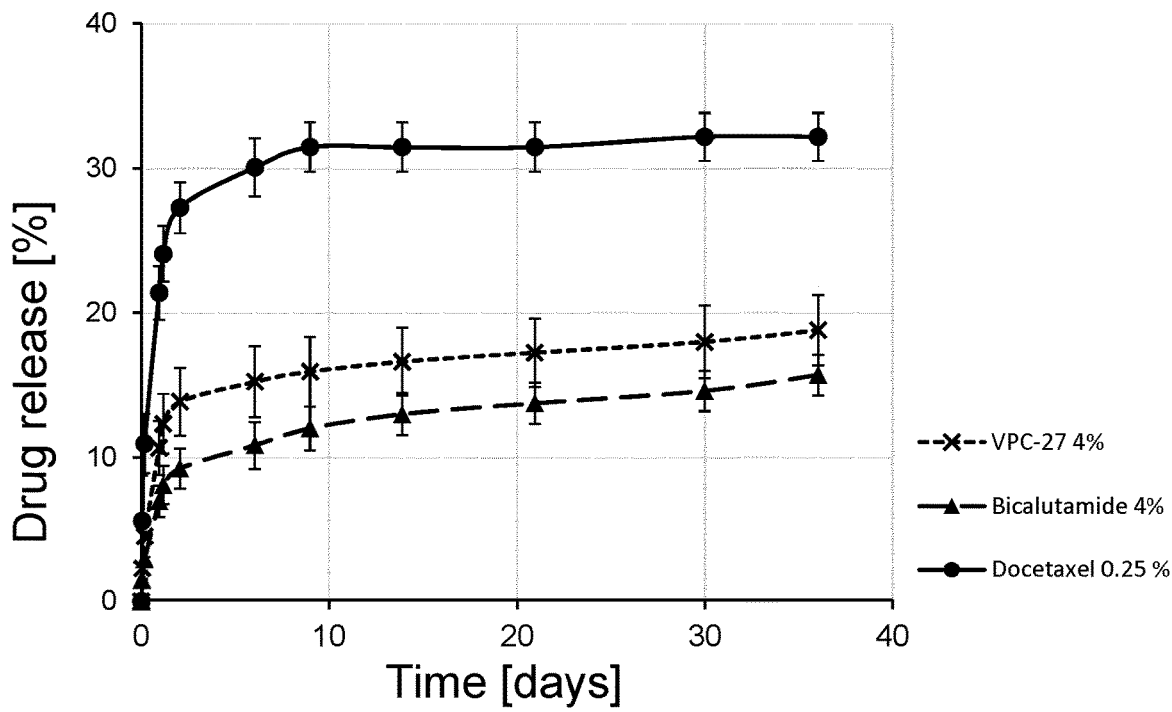
FIG. 5 shows the release of docetaxel at 0.25%, bicalutamide at 4%, and VPC-27 at 4% from PEG:PLGA:Diblock polymeric pastes (57:37:13 w/w %).
Figure 6A:
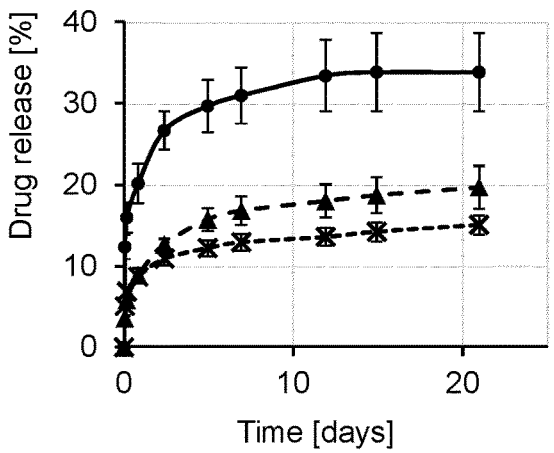
FIG. 6 shows the effect of varying PLGA:Diblock ratios (A) 43%:7%, (B) 37%:13%, (C) 31%:19% (D) 25%:25% on the release rates of docetaxel (0.5%), bicalutamide (4%), and VPC-27 (4%) from PEG:PLGA:Diblock pastes.
Figure 6B:
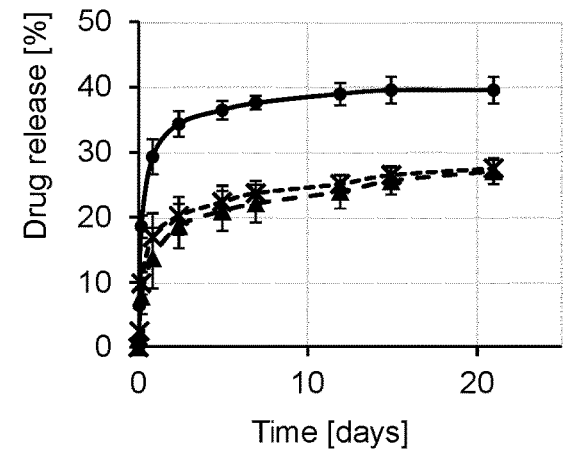
Figure 6C:
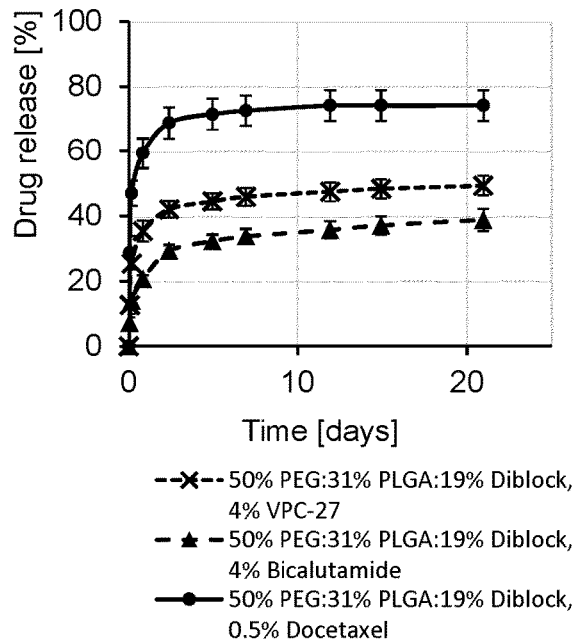
Figure 6D:
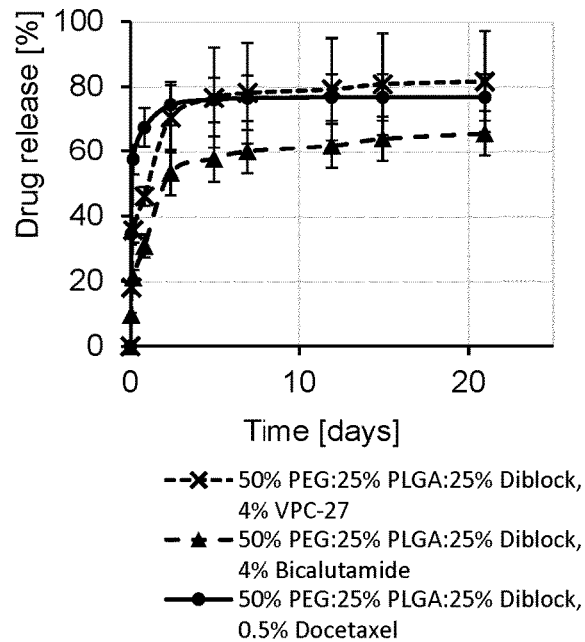

FIG. 5 shows the release of docetaxel (0.25%), bicalutamide (4%), and VPC-27 (4%) w/w from a PEG:PLGA:Diblock paste (50:37:13 w/w %). Drug release was characterized by a small burst release within the first day and a slower release of drug over the next 35 days. After one day, 24% docetaxel, 8% bicalutamide and 12% VPC-27 were released, followed by a slow release reaching 32% docetaxel, 16% bicalutamide and 19% VPC-27, on day 35 (FIG. 5).

FIG. 6 shows the effect of varying PLGA:Diblock ratios on the release rates of docetaxel (0.5%), bicalutamide (4%) and VPC-27 (4%) from PEG:PLGA:Diblock pastes (50:Y:X w/w %). Diblock (X) varied from 7, 13, 19 to 25% and PLGA (Y) varied accordingly from 43, 37, 31 to 25% w/w %.

FIG. 6 shows that by increasing diblock paste content (7%, 13%, 19%, 25%) and decreasing PLGA content, drug release rates increased. For example, at the low diblock concentration, docetaxel was released in a burst of 20% on day 1 and reached 34% on day 21 (FIG. 6A); while at the high diblock concentration, docetaxel was released in a burst of 67% on day 1 and reached 78% on day 21 (FIG. 6D). The effect was similarly pronounced for bicalutamide and more pronounced for VPC-27 (FIG. 6).

Figure 7A:
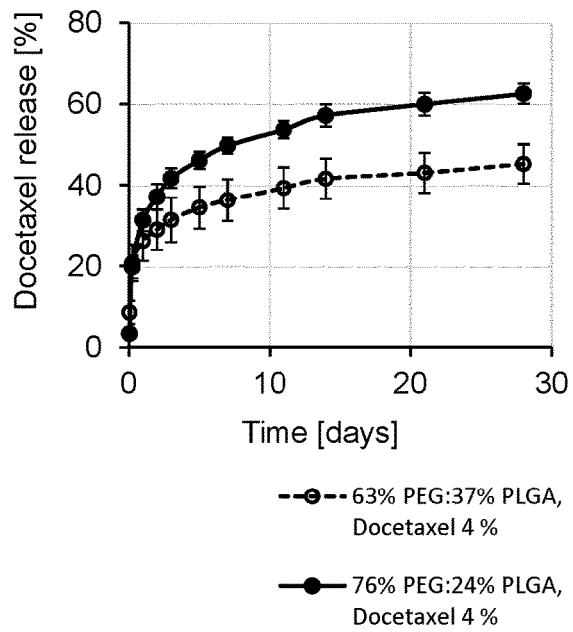
FIG. 7 shows the release of docetaxel (A), bicalutamide (B), and VPC-27 (C) from PEG:PLGA polymeric pastes (63:37 or 76:24).
Figure 7B:
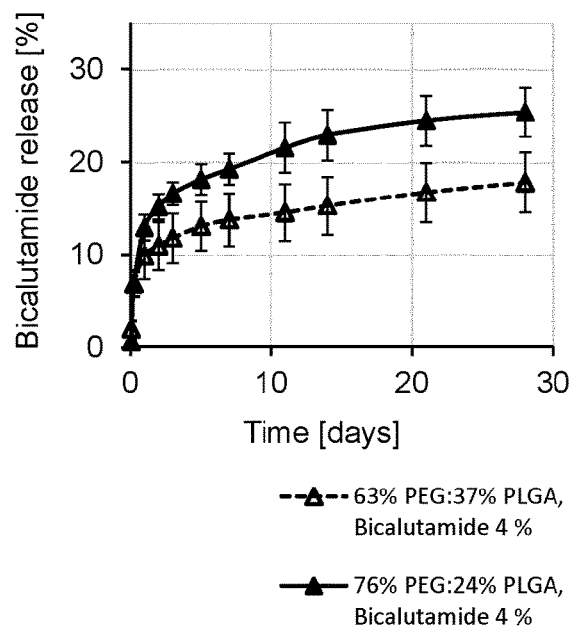

FIG. 7 shows how high amounts of PEG affects the release rates of docetaxel (4%), bicalutamide (4%) and VPC-27 (4%) from PEG:PLGA pastes (63:37 or 76:24). At too high a ratio of PEG to PLGA the paste may be very fluid and tends to disintegrate in vivo because the PLGA is over dispersed and unable to form a cohesive solid. Docetaxel released quickly from the high PEG content pastes reaching between 40% and 50% released drug at day 11 (FIG. 7A). Neither bicalutamide nor VPC-27 released quickly from either of the high PEG pastes, but release was steady and continuous even after 28 days (FIGS. 7B and 7C). At 11 days, drug release from either high PEG paste formulation was below 22% for both bicalutamide and VPC-27.

FIG. 8 shows more release profiles of docetaxel (1%), bicalutamide (4%), and VPC-27 (4%) from PEG:PLGA pastes without diblock. Three pastes were prepared with 50:50, 55:45, 60:40 PEG:PLGA (w/w %). The pastes stayed cohesive and the release of the drugs increased with increasing PEG content. The release of the three drugs in the 50:50 paste was around 2-5%, for the 55:45 paste around 10% and for the 60:40 paste between 10 and 20% on day 18.

Example 4

Release of Rapamycin from Polymeric Pastes

Polymeric pastes comprised of 50% PEG300, 37% PLGA (IV 0.15, 50:50 ratio) and 13% diblock copolymer containing a drug mixture of docetaxel, rapamycin and VPC-27 (at 1%, 1% and 4% w/w, respectively) were manufactured as described in the general methods section. Drug release experiments were performed as described previously (In vitro drug release assays, TABLE 1 and TABLE 2).

Figure 9:
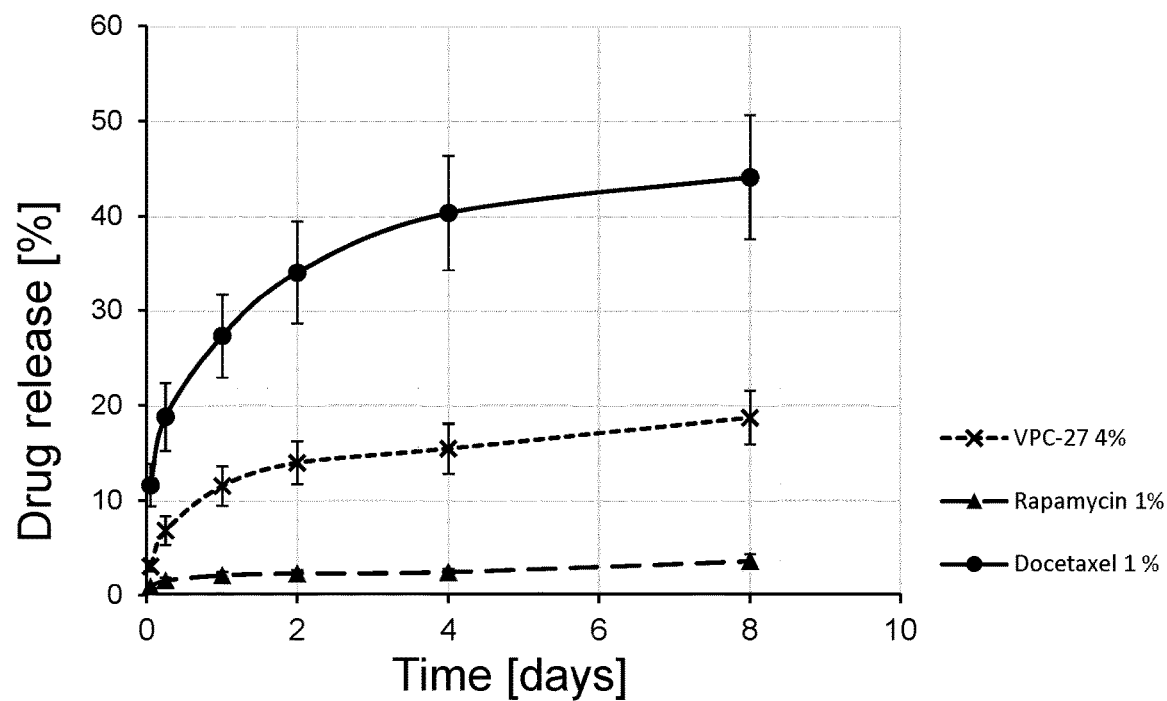
FIG. 9 shows the release of rapamycin (1%), docetaxel (1%), and VPC-27 (4%) from PEG:PLGA:Diblock polymeric pastes (50:37:13 w/w %).

FIG. 9 shows the release rates for docetaxel, rapamycin, and VPC-27, from PEG:PLGA:Diblock pastes (50:37:13). Docetaxel released in a sustained manner reaching almost 45% drug release at day 8. VPC-27 released well, reaching almost 20% release at day 8. Rapamycin released very slowly with only 4% of the encapsulated drug being released at day 8.

Example 5

Release of Cephalexin from Polymeric Paste

Figure 10A:
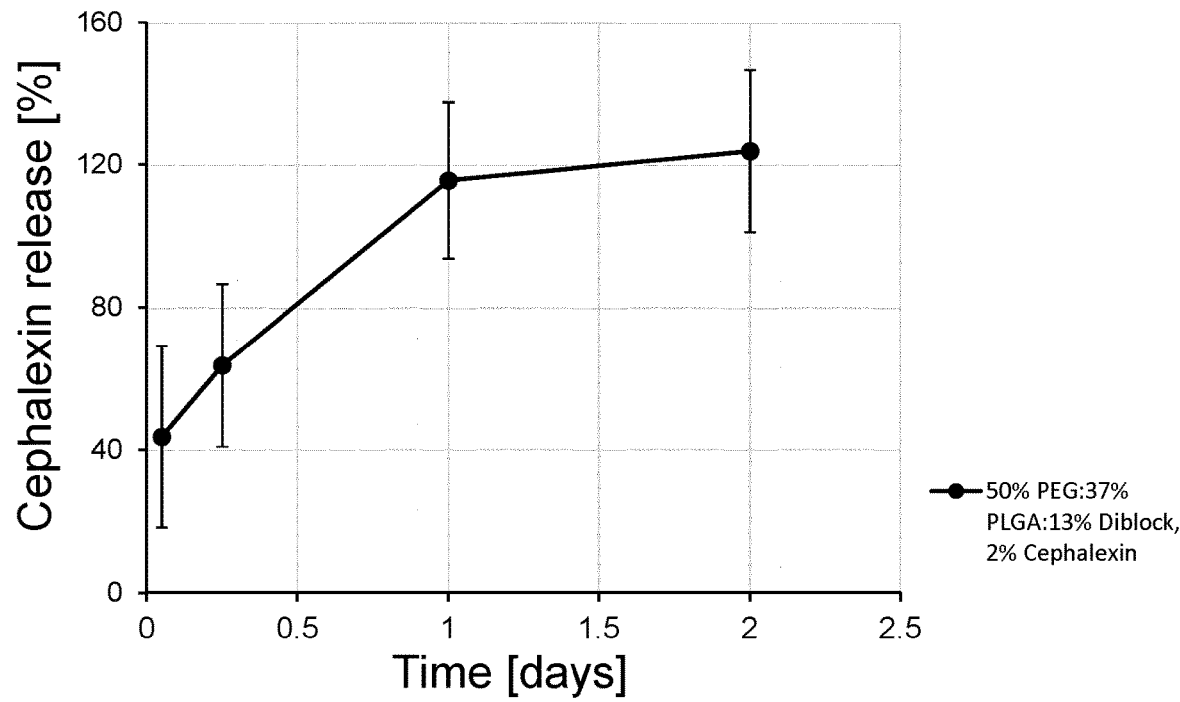
FIG. 10 shows the release of Cephalexin (A) 2% and (B) 4%, 6%, 8% and 10% from PEG:PLGA:Diblock polymeric paste (50:37:13 w/w %).
Figure 10B:
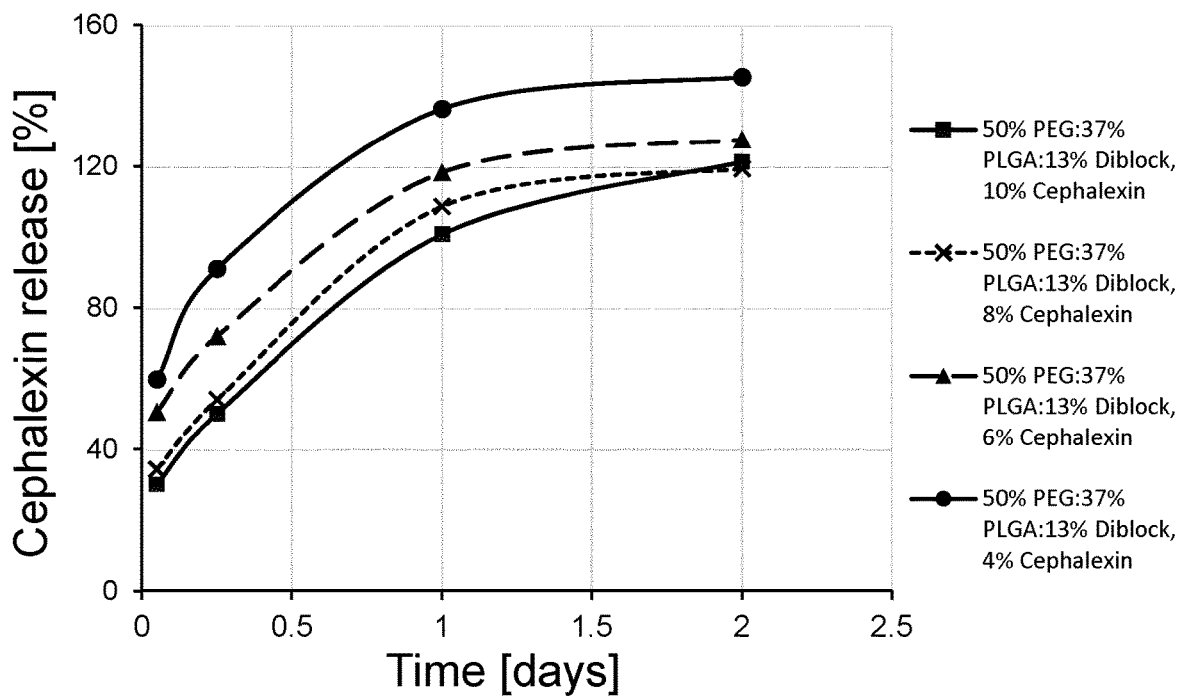

Polymeric pastes comprised of 50% PEG300, 37% PLGA (IV 0.15, 50:50 ratio) and 13% dibock copolymer containing cephalexin at between 2 and 19% loading were prepared as described in Examples 1 and 3. For cephalexin, albumin was not included in the PBS as this drug is water soluble. The drug release was studied according to the descriptions found in the general methods section (In vitro drug release assays, TABLE 1 and TABLE 2). FIG. 10 shows that Cephalexin released quickly from the polymeric pastes where almost all drug was released from drug loaded pastes at 1 day.

Example 6

Effect of Paste Geometry and Drug Loading on the Release of Lidocaine from Polymeric Paste PEG:PLGA:Diblock paste (50:37:13) containing lidocaine (non-HCl form) at 2-10% w/w loading were mixed as previously described. To achieve different paste geometries, the 8% w/w paste was placed in a syringe and 100 mg samples were extruded through an 18 gauge needle onto the base of a cold (approximately 2° C.) 20 ml glass scintillation vial as either a cylinder, a crescent shape in the lower corner of a tilted vial or as a hemisphere "blob" in the middle of the base of the vial. The cold temperature assisted in keeping the shape of the very viscous paste at this temperature. 10 ml of cold PBS were very gently added and the vial was left for 10 minutes to allow the outer surface of the paste to whiten a little. The vials were then placed in a 37° C. incubator. At dedicated time points the 10 ml of PBS were removed and replaced with another 10 ml of room temperature PBS. The drug release was studied according to the descriptions found in the general methods section (In vitro drug release assays, TABLE 1 and TABLE 2).

Figure 11A:
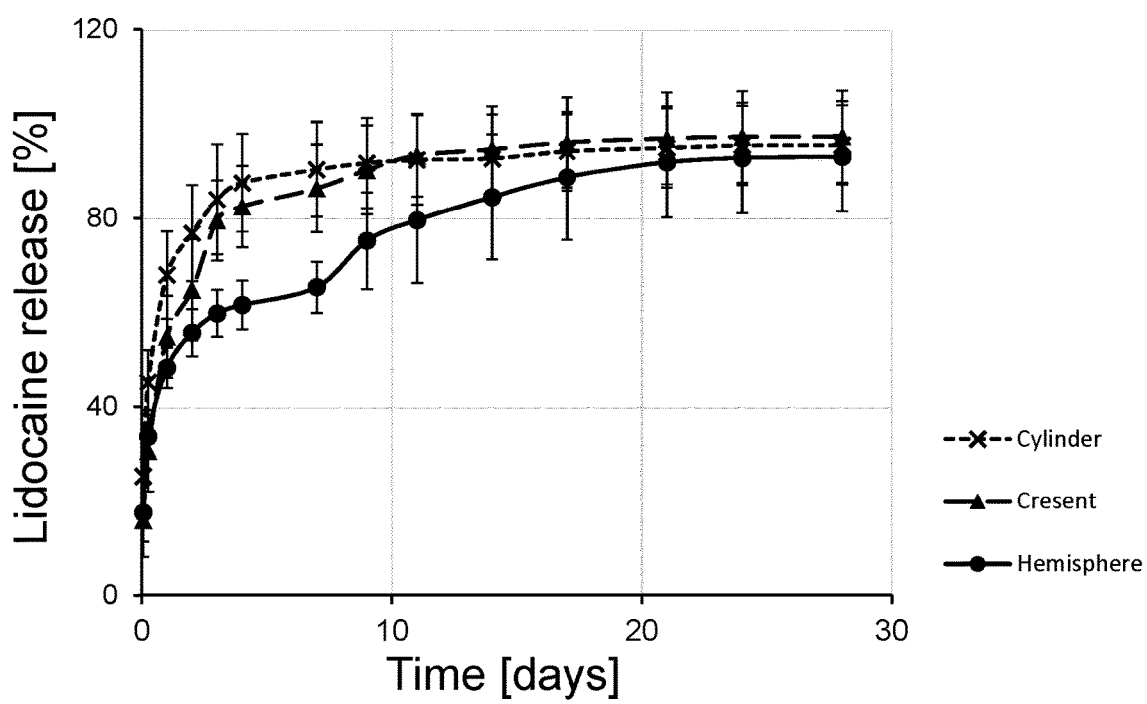
FIG. 11 shows the release of lidocaine from various paste shapes (cylinder, crescent and hemisphere (A)) and at different lidocaine concentrations (2%, 4%, 6%, 8% and 10% (B)) from PEG:PLGA:Diblock polymeric paste (50:37:13 w/w %).
Figure 11B:
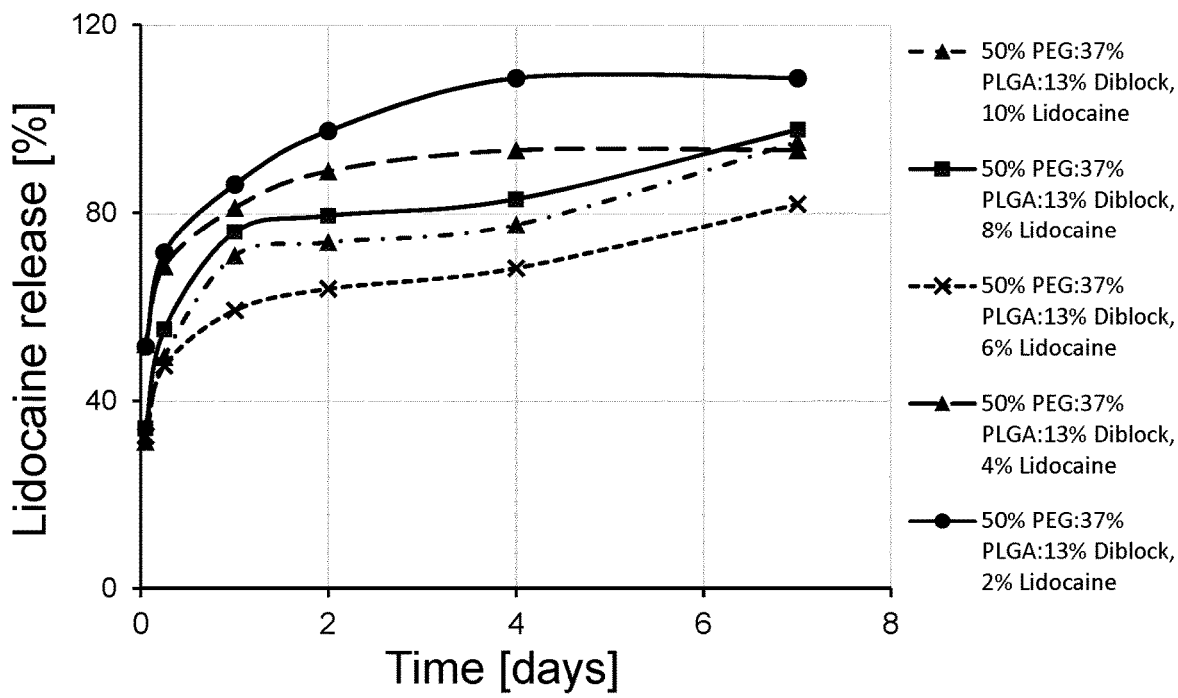

Lidocaine released from all geometric forms with a burst phase between approximately 50% and 70% at day 2 (FIG. 11A). After that the release rate slowed, especially for the hemisphere shape, such that by day 7 this shape had released approximately 65% of the drug as compared to 88% and 92% released from the crescent and cylinder shapes, respectively. All paste shapes released small amounts of lidocaine between 7 to 28 days. The release rates for lidocaine using different % w/w loadings were similar and are shown in FIG. 11B.

Example 7

Release of Docetaxel, VPC-27 and Enzalutamide from Polymeric Pastes

Figure 12A:
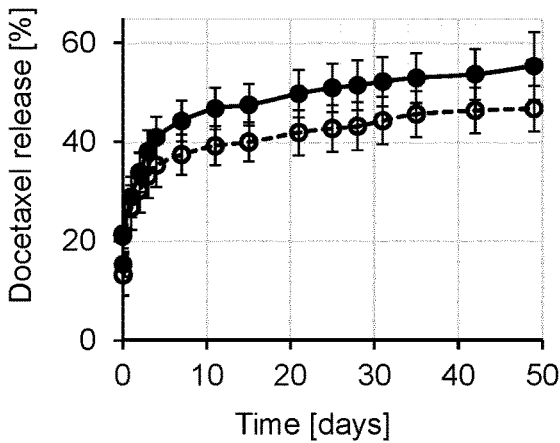
FIG. 12 shows the release of 1% docetaxel (A), 4% Enzalutamide (B), or 4% VPC-27 (C) from PEG:PLGA:Diblock polymeric pastes (63:37 w/w % or 50:37:13 w/w %).
Figure 12B:
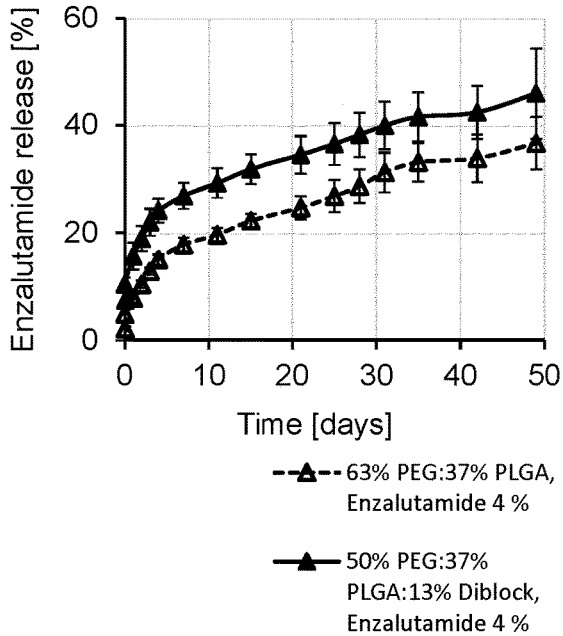
Figure 12C:
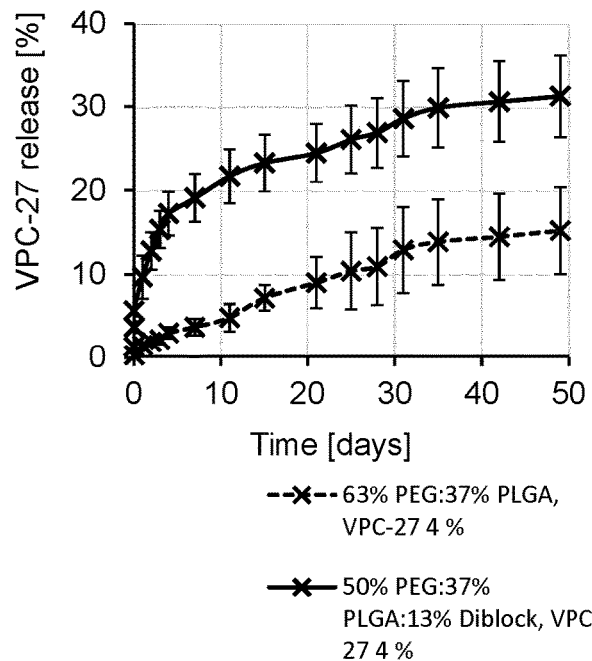

Polymeric pastes were manufactured from 63:37 compositions of PEG 300™ and PLGA (50:50 IV=0.15) or from 50:37:13 ratios of PEG:PLGA:Diblock using the method described earlier. The drugs VPC-27, enzalutamide or docetaxel were added at various weight ratios directly into the paste with mixing by standard spatula levigation techniques. The drug release was studied according to the descriptions found in the general methods section (In vitro drug release assays, TABLE 1 and TABLE 2). All drugs released more quickly from the diblock containing paste than the high PEG content paste as shown in FIG. 12. From the high PEG content PEG:PLGA paste (63:37), VPC-27 released slowly without any apparent burst phase of release (FIG. 12C) but a burst phase occurred from the PEG:PLGA:diblock containing paste (50:37:13), resulting in nearly 35% of drug released by day 50 (FIG. 12C). Docetaxel released well from both pastes (approximately 50% released by day 50) (FIG. 12A) and enzalutamide released approximately 40% of the total encapsulated drug by day 50 (FIG. 12B).

Example 8

Solubilization of Drugs by Diblock Copolymer

Figure 13:
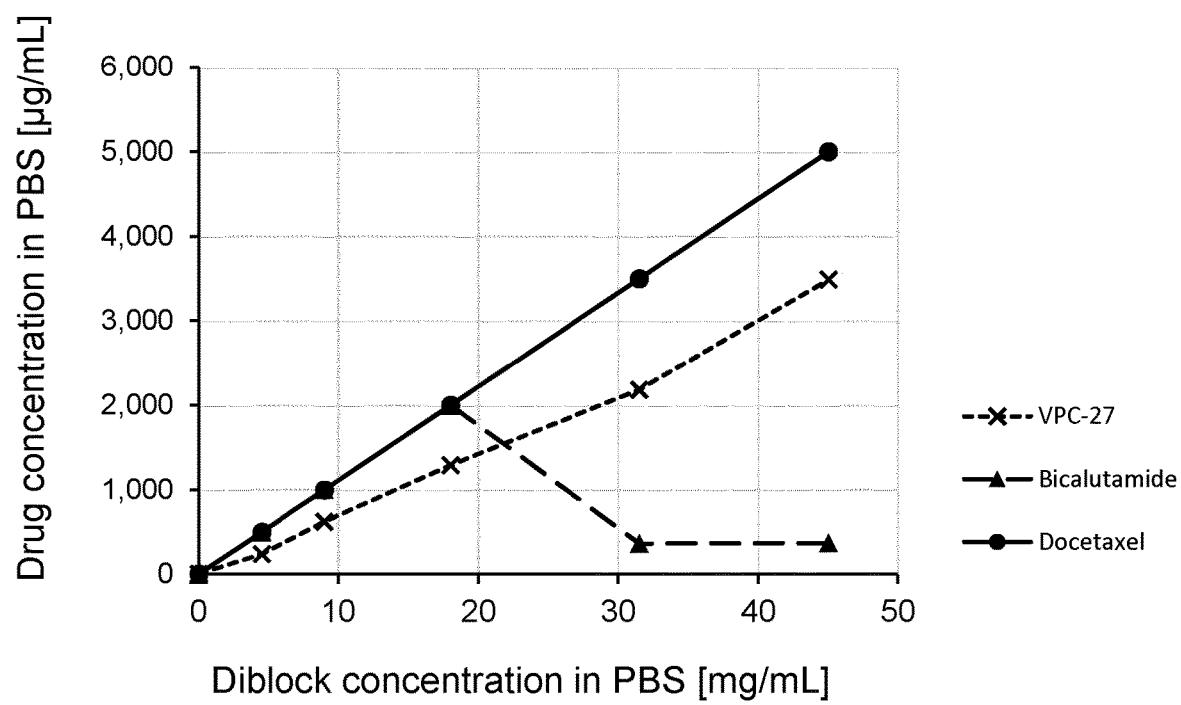
FIG. 13 shows the solubilization of docetaxel, bicalutamide, or VPC-27 by diblock copolymer (molecular weight 3333, PLLA 40%, MePEG 2000 60%).

Diblock copolymer (molecular weight 3333, PLLA 40%, MePEG 2000 60%) was weighed out into 2 ml glass vials in various amounts at concentrations of 0 to 45 mg/ml. The drugs docetaxel, bicalutamide, and VPC-27 were added in a drug polymer ratio of 1:9 (one part drug, 9 parts diblock copolymer) from stock solutions in acetonitrile and topped up to approximately 1 ml. All contents were in solution and the vials were dried down under nitrogen with mild heat followed by vacuum overnight. The vials were then warmed to 37° C. and 1 ml of PBS at 37° C. was added. The vials were vortexed to dissolve their contents and the contents were then centrifuged at 15000 rpm in a microfuge and filtered through a 0.2 μm filter to give a clear solution. The concentration of each drug in each solution was then measured using RP-HPLC described in the general methods section (In vitro drug release assays, TABLE 1 and TABLE 2). Drugs were solubilized effectively by the diblock copolymer as shown in FIG. 13. For VPC-27 and docetaxel, drug concentrations in the 3.5 to 5 mg/ml range were achieved. Above a diblock concentration of 20 mg/ml, bicalutamide did not stay in solution as shown in FIG. 13.

Example 9

Release of Lidocaine (10%) and Desoximetasone (1%) from PEG:PLGA:Diblock Paste (50:37:13

The paste was manufactured as in Example 7 using lidocaine at 10% and desoximetasone at 1%. Drug release was measured using RP-HPLC as described earlier (In vitro drug release assays, TABLE 1 and TABLE 2).

Figure 14:
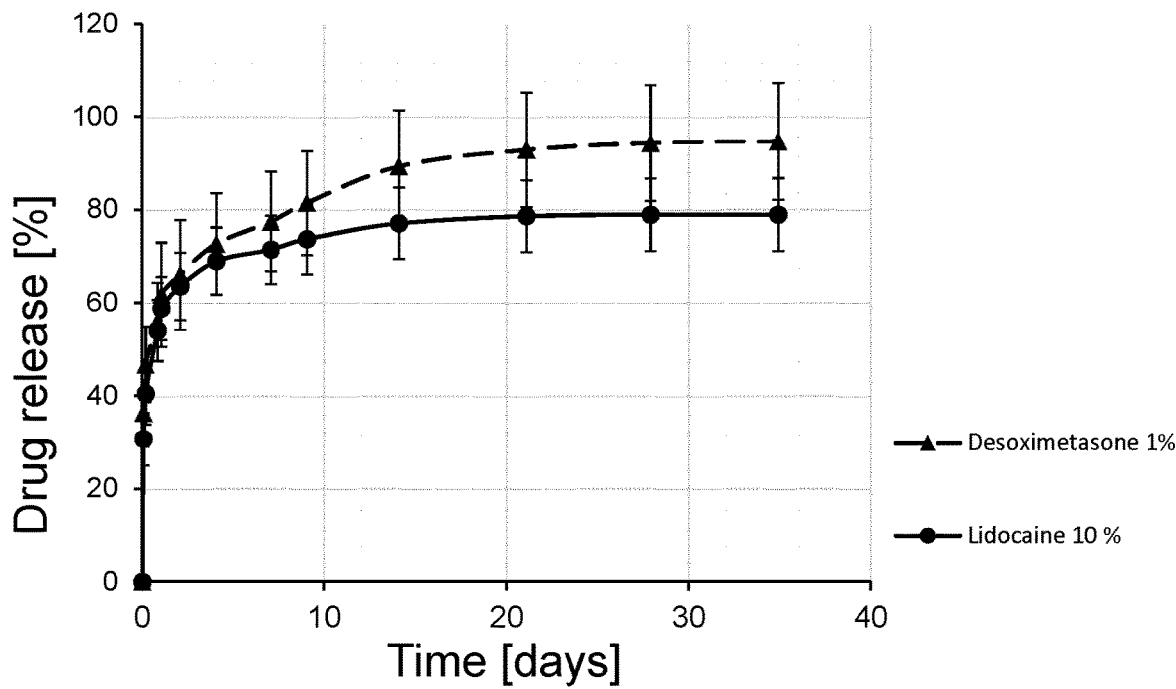
FIG. 14 shows the release of lidocaine (10%) and desoximetasone (1%) from PEG:PLGA:Diblock polymeric paste (50:37:13 w/w %).

FIG. 14 shows that lidocaine released in the same manner as previously observed with a 50% burst within the first day and an extended release reaching 80% by day 35. Similarly, desoximetasone released with a burst of 50% on day one and reached 100% release on day 35. The injectable lidocaine pastes keep the drug near the local injection site and delays systemic uptake of lidocaine. The suggested drug load is 10% and the maximum injectable volume should be 3 g of paste into the spermatic cord to stay below the maximum single dose of 300 mg. Lidocaine is released in a sustained fashion while the paste degrades.

Example 10

Release of Lidocaine from Various PEG:PLGA Pastes without Diblock

Figure 15:
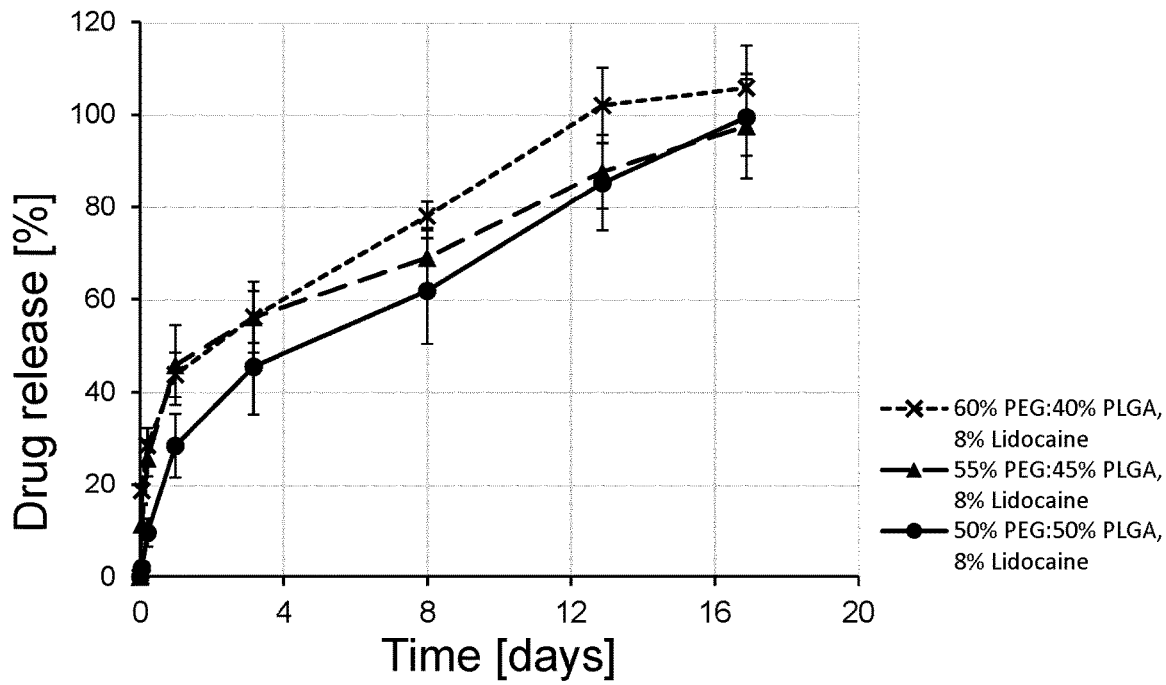
FIG. 15 shows the release of lidocaine (8%) from PEG:PLGA pastes (50:50, 55:45 and 60:40).

Pastes were manufactured as described in Example 1. FIG. 15 shows the lidocaine release from PEG:PLGA pastes without diblock. Three pastes were prepared with 50:50, 55:45, 60:40 PEG:PLGA (w/w %) and 8% lidocaine (w/w). The pastes stayed cohesive and drug release was faster in pastes with higher PEG content. Lower PEG content decreased the amount of burst release slightly and by day 18, 100% of lidocaine was released from all pastes.

Example 11

Release of Sunitinib from PEG:PLGA:Diblock Polymeric Paste (50:37:13

Figure 16:
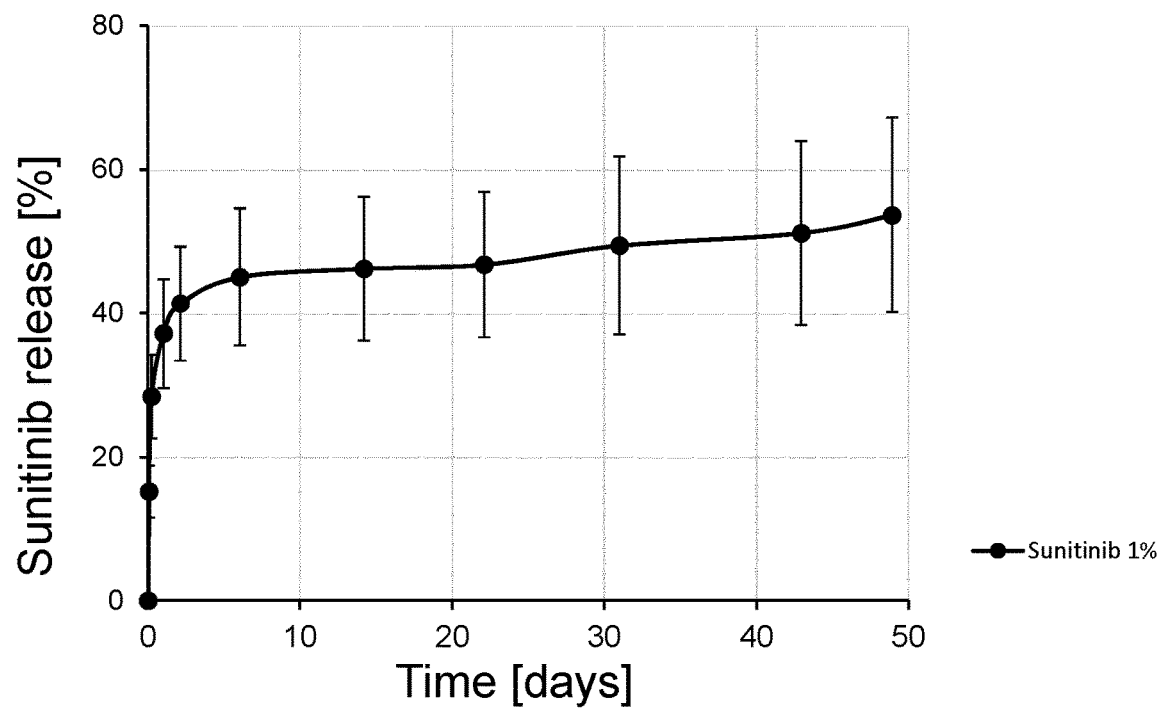
FIG. 16 shows the release of sunitinib (1%) from PEG:PLGA:Diblock polymeric paste (50:37:13 w/w %).

The paste was manufactured as in Example 7 and the drug Sunitinib was added at 1% w/w. Drug release was measured using RP-HPLC as described earlier (In vitro drug release assays, TABLE 1 and TABLE 2). The release of Sunitinib is shown in FIG. 16 and is characterized by a burst phase on day 1 with a release of 35% and an extended release phase that reaches approximately 55% at day 44.

Example 12

Release of Tamsulosin from PEG:PLGA:Diblock Polymeric Paste (50:37:13

Figure 17:
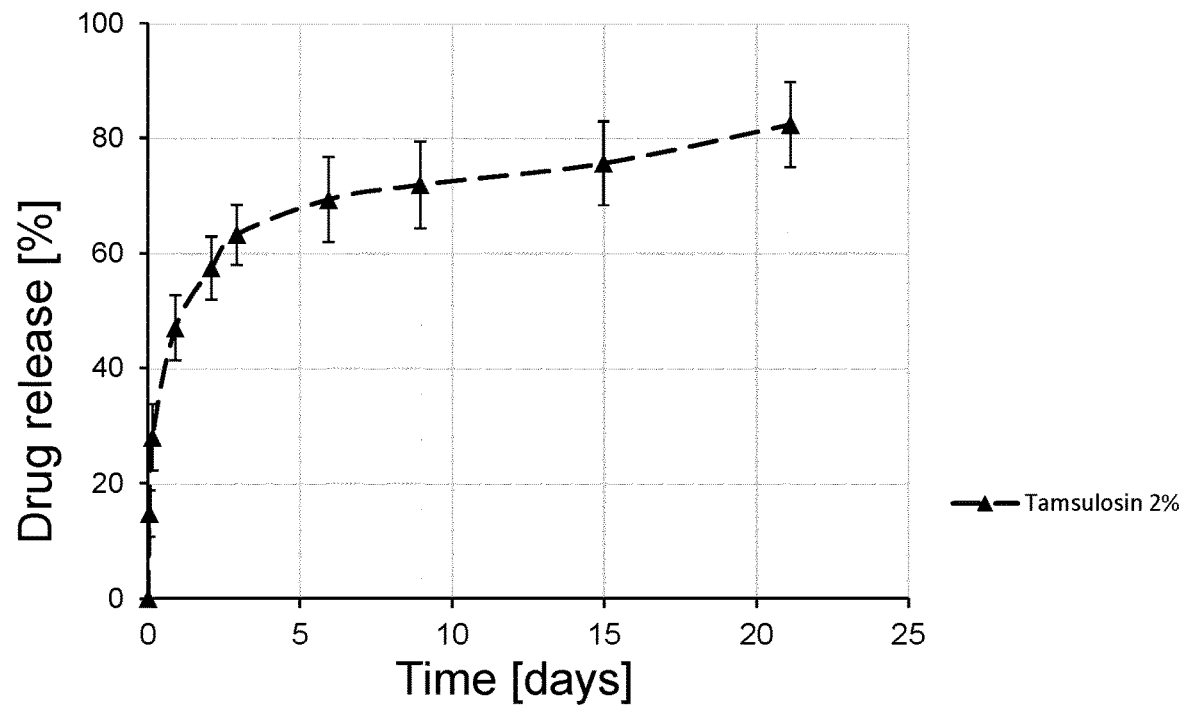
FIG. 17 shows the release of Tamsulosin (2%) from PEG:PLGA:Diblock polymeric paste (50:37:13 w/w %).

Tamusolin was loaded at 2% w/w to PEG:PLGA:Diblock polymeric paste (50:37:13 PEG:PLGA:Diblock) as described in Example 6. Drug release was measured using RP-HPLC as described earlier (In vitro drug release assays, TABLE 1 and TABLE 2). The release of Tamsulosin is shown in FIG. 17 and is characterized by a burst phase of 47% on day 1. The release continues and reaches 70% by day 6 and 80% on day 21.

Example 13

Release of Lidocaine (8%), Cephalexin (2%) and Ibuprofen (5%) from PEG:PLGA:Diblock Polymeric Paste (50:37:13

Figure 18:
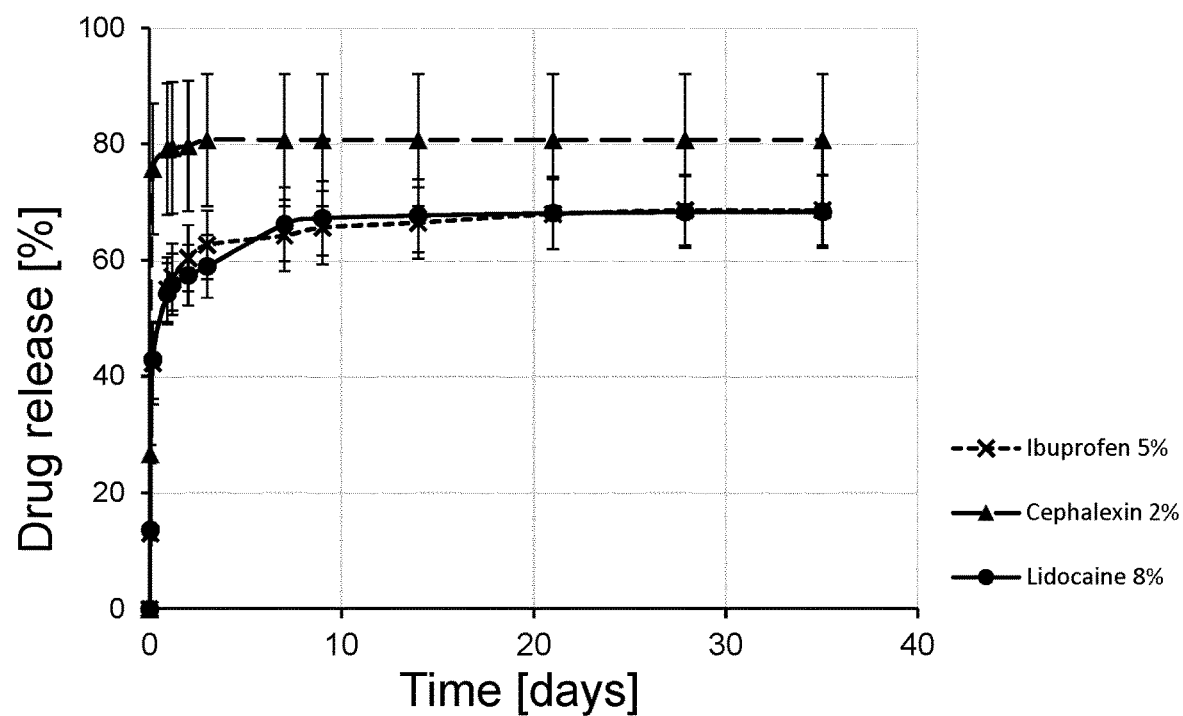
FIG. 18 shows the release of lidocaine (8%), cephalexin (2%), and ibuprofen (5%) from PEG:PLGA:Diblock polymeric paste (50:37:13 w/w %).

The three drugs were loaded into the paste as previously described in Example 3. HPLC analysis for lidocaine, cephalexin and ibuprofen was performed using the general chromatographic set up mentioned earlier (In vitro drug release assays, TABLE 1 and TABLE 2). The release of the three drugs is shown in FIG. 18. Cephalexin was released very quickly and reached its maximum at 80% on day 3. Lidocaine and Ibuprofen release was similar and characterized by a burst release of 54% drug by day one and a slower drug release over the next 10 to 15 days, reaching approximately 70% by day 35.

Example 14

Figure 19A:
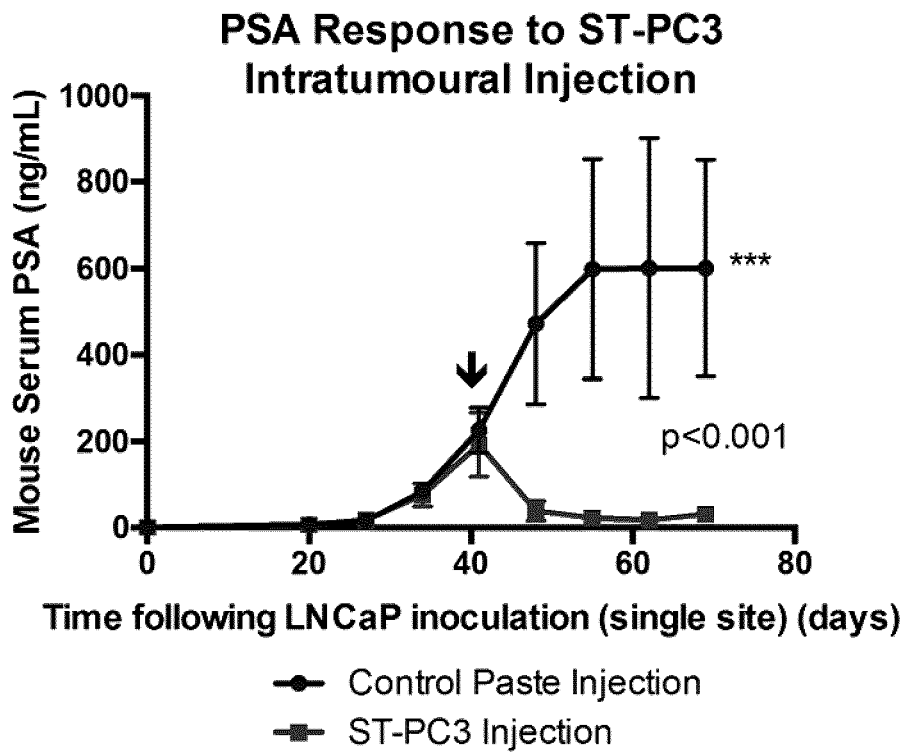
FIG. 19 shows the effect of drug-loaded (i.e. docetaxel (1%), bicalutamide (1%), and VPC-27 (4%)) PEG:PLGA:Diblock polymeric paste (50:37:13 w/w %) versus control paste (i.e. no drug) on mouse serum PSA (A) and absolute tumour size (B) as a representation of human prostate cancer tumors (ST-PC3) in mice. A study to determine the effect of variable concentrations of docetaxel.
Figure 19B:
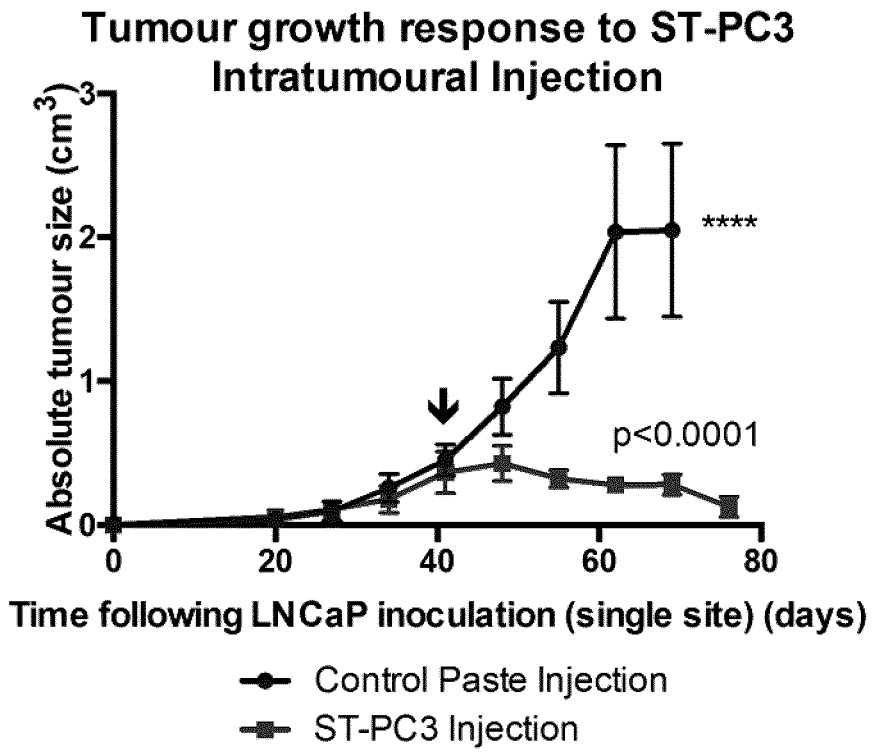
Figure 20A:
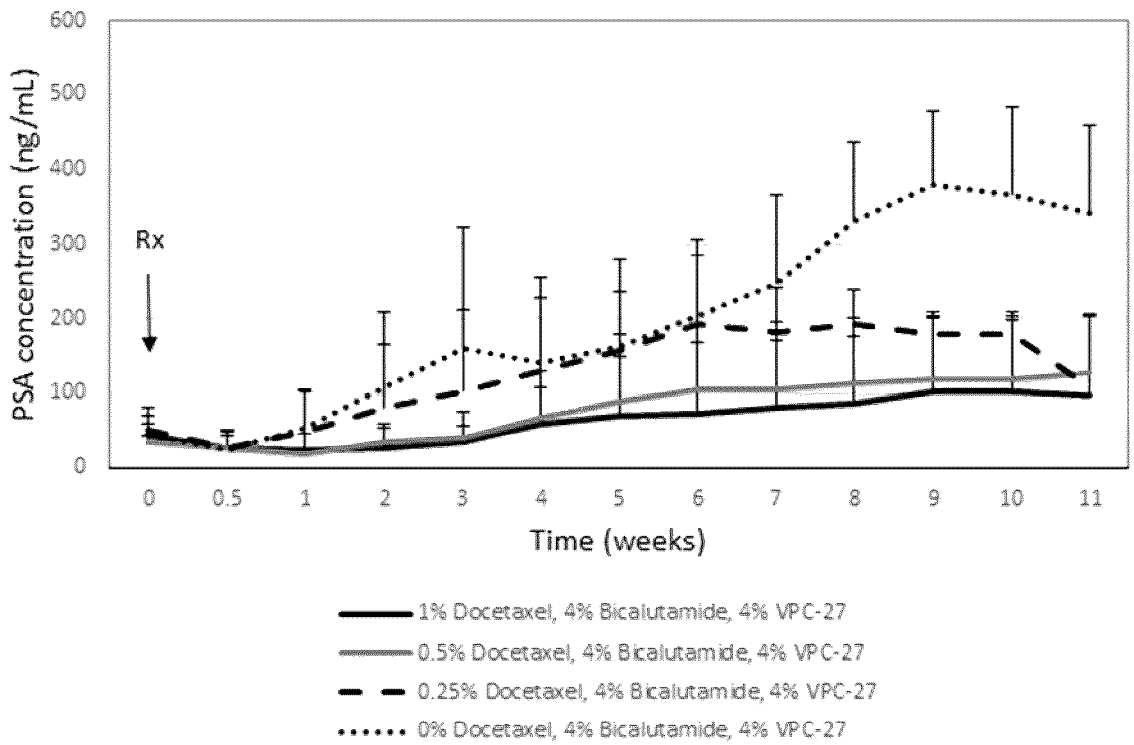
FIG. 20 shows the effect of varied amounts of Docetaxel (i.e. 0%, 0.25%, 0.5% and 1%) drug-loaded (i.e. Bicalutamide (4%), and VPC-27 (4%) PEG:PLGA:Diblock polymeric paste (50:37:13 w/w %) on mouse serum PSA (A) and absolute tumour size (B) as a representation of human prostate cancer tumors in mice.
Figure 20B:
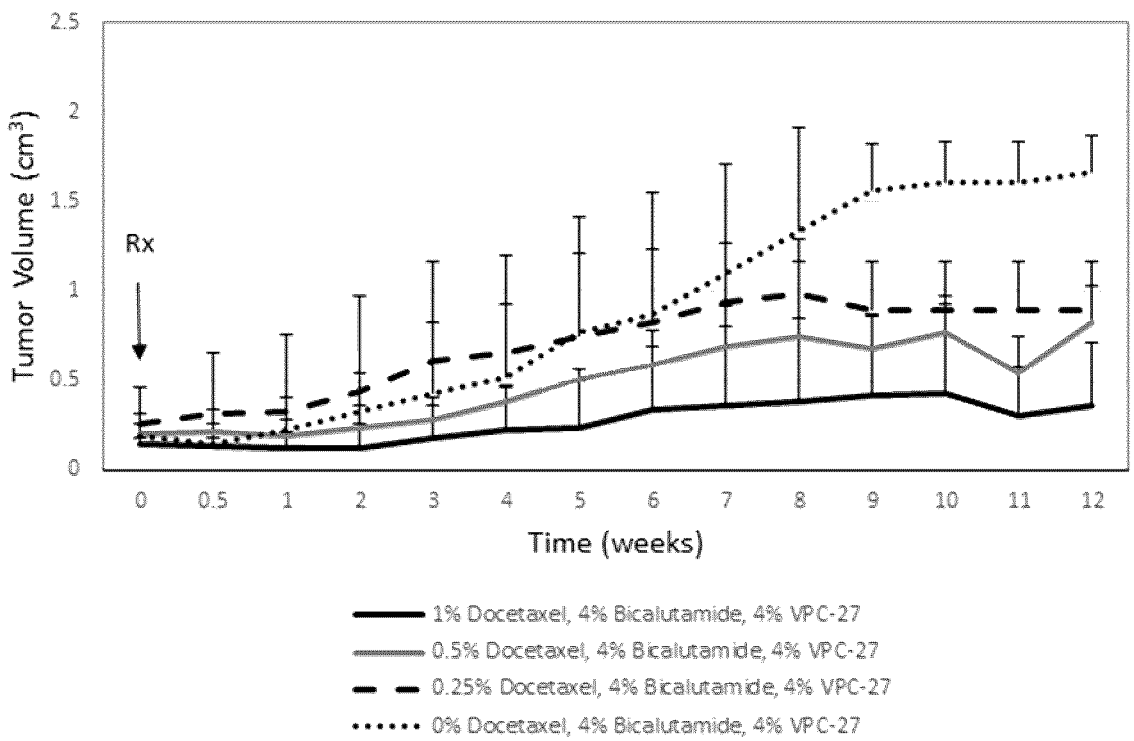
Figure 21A:
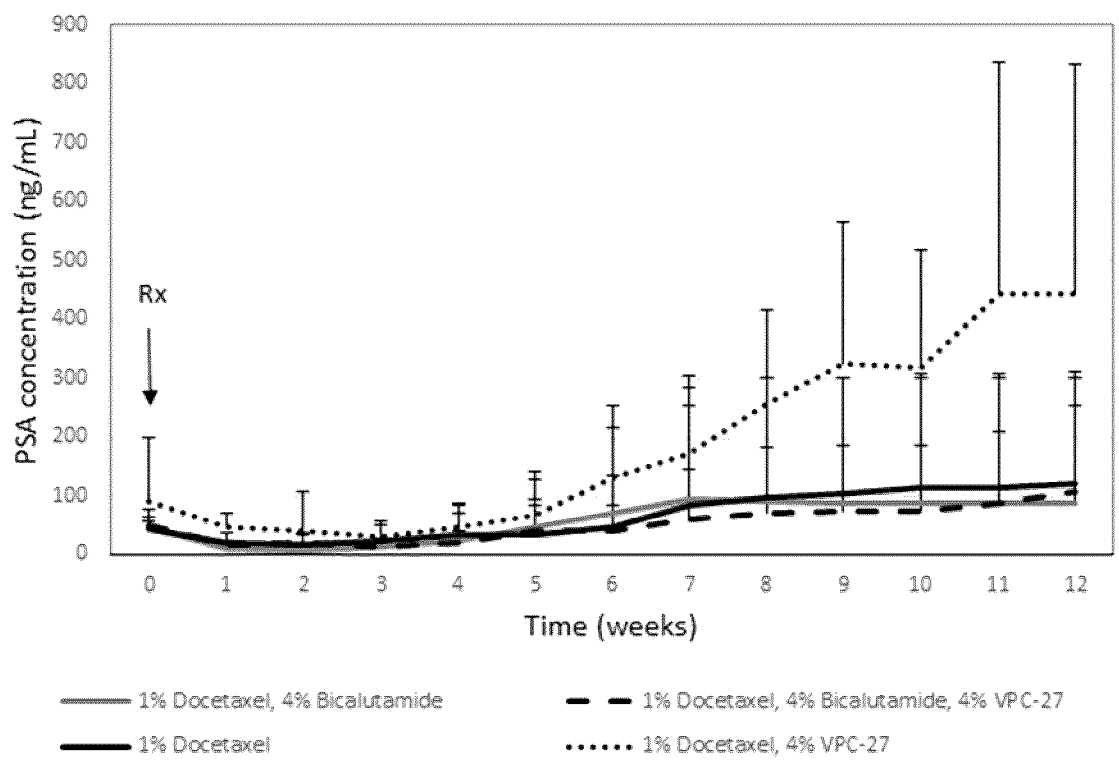
FIG. 21 shows serum PSA concentrations (A) and tumour volume in cm$^3$ (B) after intratumoral injection of drug-loaded pastes (1% Docetaxel and 4% Bicalutamide; 1% Docetaxel, 4% Bicalutamide and 4% VPC-27; 1% Docetaxel; and 1% Docetaxel and 4% VPC-27).
Figure 21B:
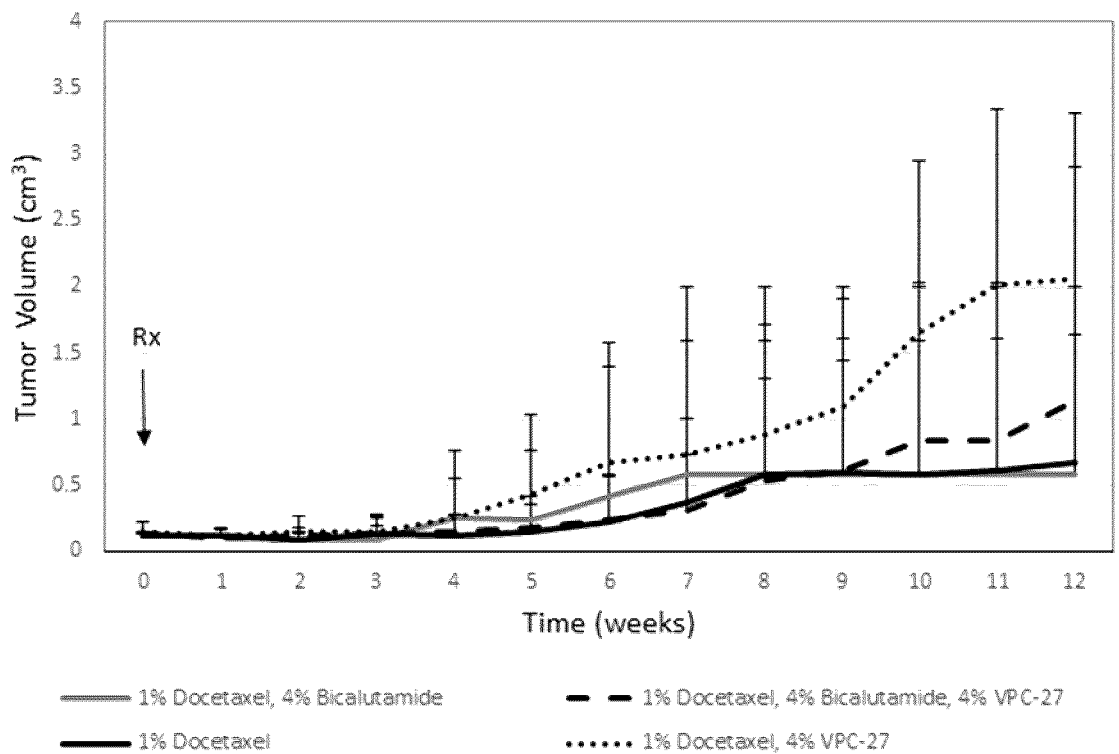

Effect of Drug Loaded Polymeric Paste on the Growth of Human Prostate Cancer Tumors in Mice PEG:PLGA:Diblock polymeric paste (50:37:13) containing docetaxel (1%), bicalutamide (1%), and VPC-27 (4%) was manufactured as previously described and injected intra-tumorally (see Intratumoral paste injection, FIG. 19).

In a different experiment, groups of mice were treated with a formulation containing either docetaxel alone, bicalutamide and docetaxel, docetaxel and VPC-27 or all three drugs. Treatment groups that received both docetaxel and bicalutamide or docetaxel alone showed slower tumor growth and a delayed increase in serum PSA levels than groups that received pastes that contained also VPC-27.

Example 16

Local Release of Lidocaine and Absence from Serum In Vivo

Five groups of rats (male, Sprague Dawley) with six animals in each group received one injection of paste formulation (0.1 mL) subcutaneously in their flank. The paste formulation was based on a 50:50 mixture of PEG 300™ and PLGA. Lidocaine was incorporated into the paste at 80, 100, 120, 140, and 160 mg per g of paste. The corresponding doses for each group were 23, 29, 36, 40 and 45 mg of lidocaine per kg. Lidocaine dissolved at all concentrations to form a clear paste except at the 160 mg/g level, where small crystals were visible that dissolved when warming the paste to 37° C. All formulations were warmed to 37° C. before administration and the injection was smooth.

Figure 22A:
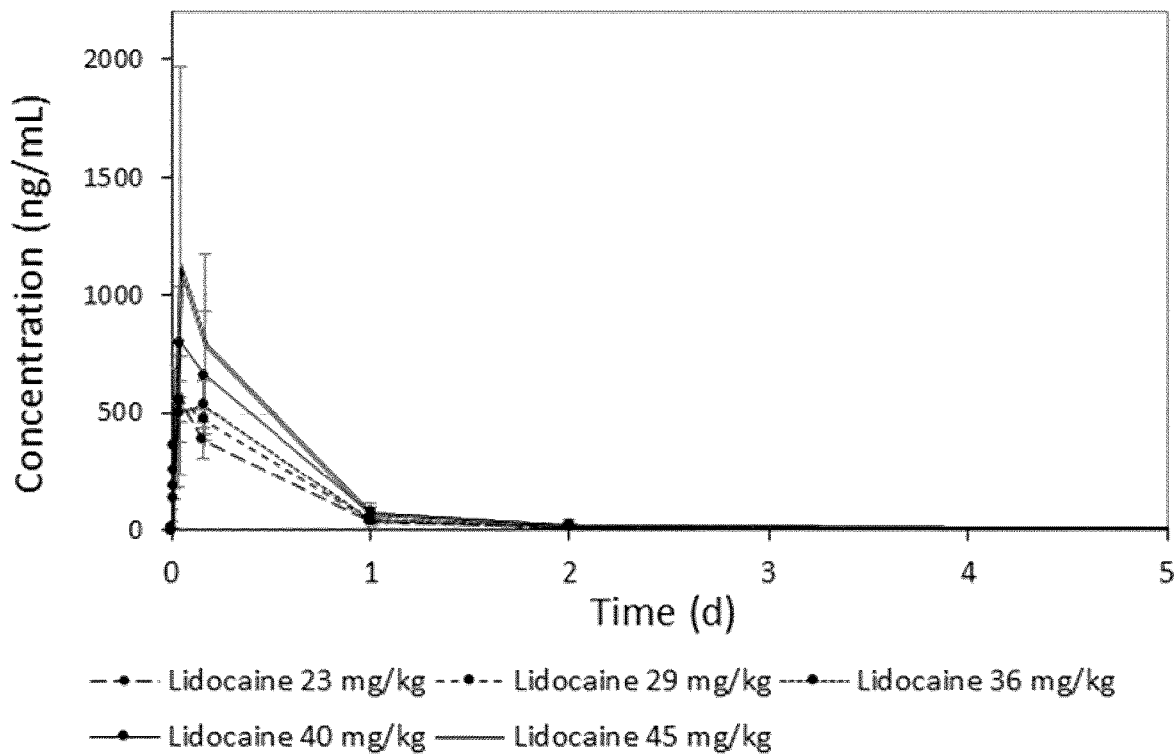
FIG. 22 shows the systemic absorption of lidocaine after local injection of lidocaine pastes (in PEG/PLGA 50/50) subcutaneously in rats at different doses of lidocaine paste (i.e. 23 mg/kg; 29 mg/kg; 36 mg/kg; 40 mg/kg; and 45 mg/kg) as a measure of serum concentration observed over time (A) and as a semi logarithmic plot (B).
Figure 22B:
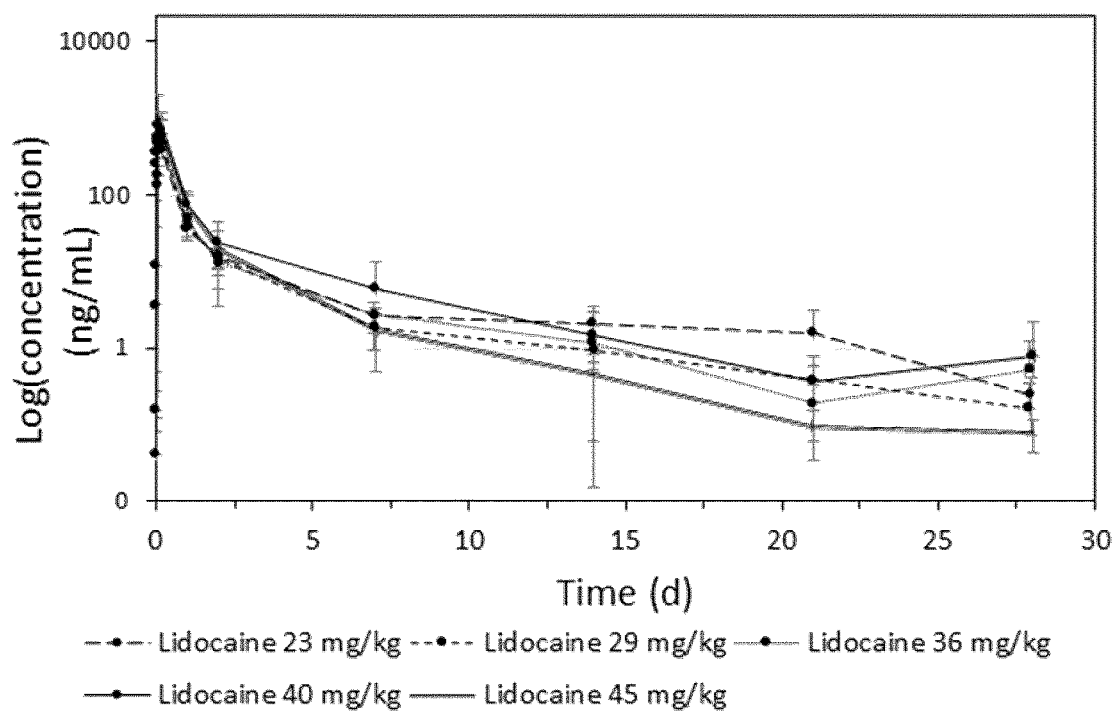

The concentrations of systemic lidocaine detected in serum were very low (see FIGS. 22A and 22B). The maximum concentrations detected in serum in each group were all below the upper limit of its therapeutic range of 5 µg/mL or 5000 ng/mL in all studied strengths. The maximum serum concentrations for the 80, 100, 120, 140, 160 mg/g paste formulations were 557.26±81.15, 578.90±162.59, 638.03±190.61, 855.98±196.18, 1148.88±838.97 ng/mL respectively. Since the highest dosing level (160 mg/g paste or 45 mg/kg) is 10 times above the locally administered lidocaine dose in humans (4.5 mg/kg) using a conventional lidocaine solution.

Example 17

Use of Swelling Agents in Paste

Pastes were manufactured using 68% PEG 300™, 30% PLGA and 2% of a swelling agent. The agents included carboxymethylcellulose, carbomer or sodium hyaluronate. These pastes were effectively injected through a 5 F ureteral catheter of 70 centimeters length. In water there was a clearly observed swelling behavior.

Figure 25A:
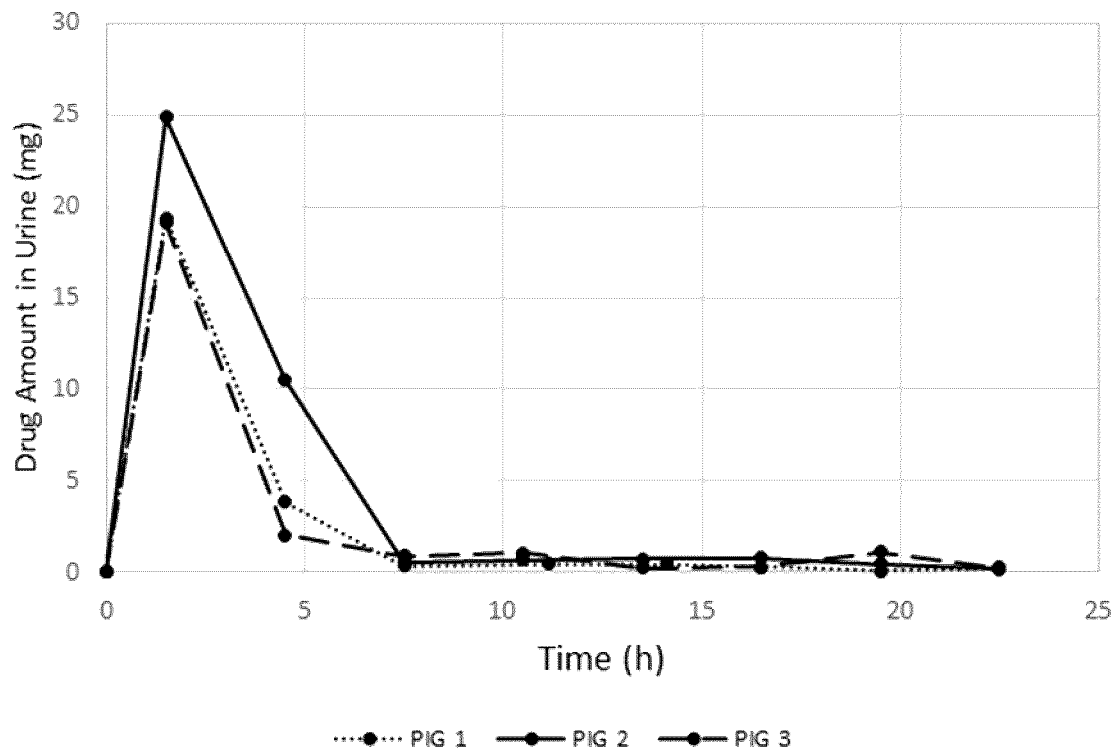
FIG. 25 shows the urinary excretion after injection of 5% gemcitabine pastes into pig kidney pelvis (A) and serum gemcitabine concentrations after injection of 5% gemcitabine pastes (68% PEG: 30% PLGA) into pig kidney pelvis (B) to show systemic absorption of gemcitabine paste containing a swelling agent (2% SH) in three pigs (administration of 1.5 mL of a 5% gemcitabine paste into kidney pelvis using 5 F ureteral catheter).
Figure 25B:
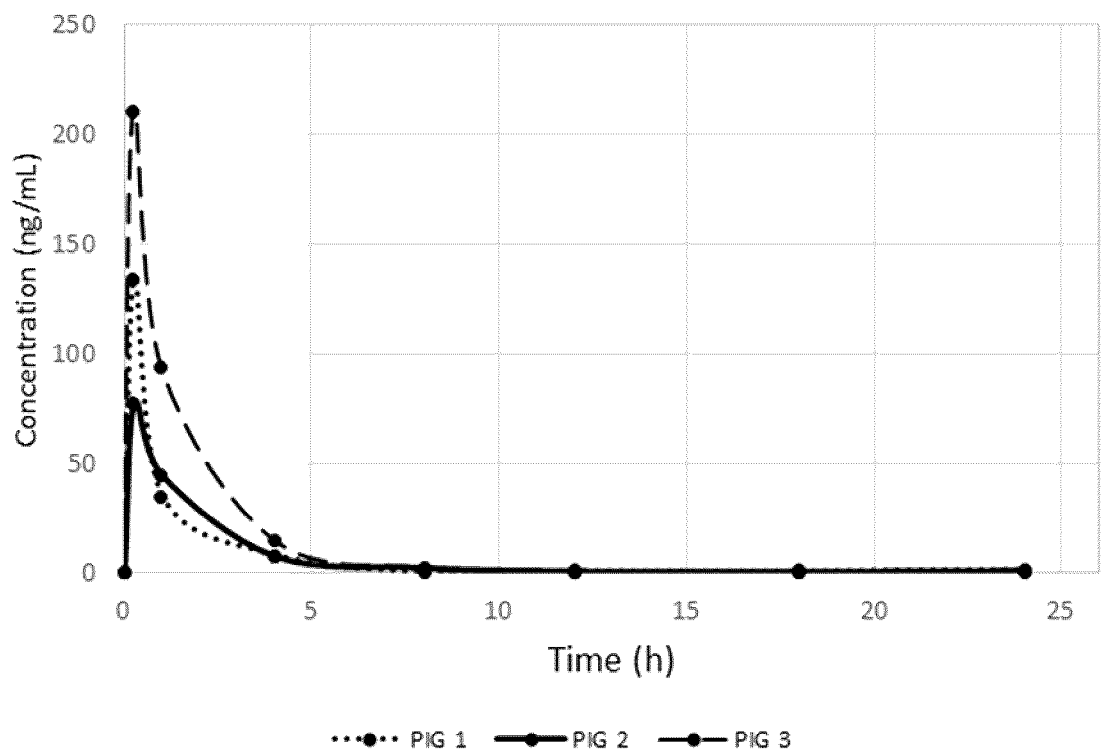

The drug gemcitabine was incorporated at 5% (m/m) in the sodium hyaluronate containing paste. This paste was injected through the 5 F catheter into the kidney pelvis of a pig. Gemcitabine levels in urine were initially high and levelled off after 5-7 hours (see FIG. 25A). Serum gemcitabine levels were very low, but detectable in all pigs (see FIG. 25B). The paste did not result in any blockage of the ureter and paste fragments were found on the urinary catheter after removal.

Example 18

Use of Swelling Agent, Sodium Hyaluronate, for Gemcitabine Release

Pastes containing 2% of sodium hyaluronate (SH) and increasing amounts of diblock copolymer were prepared to observe swelling and degradation of these pastes over one hour. The inclusion of SH was associated with a rapid swelling of the paste in water.

Figure 23:
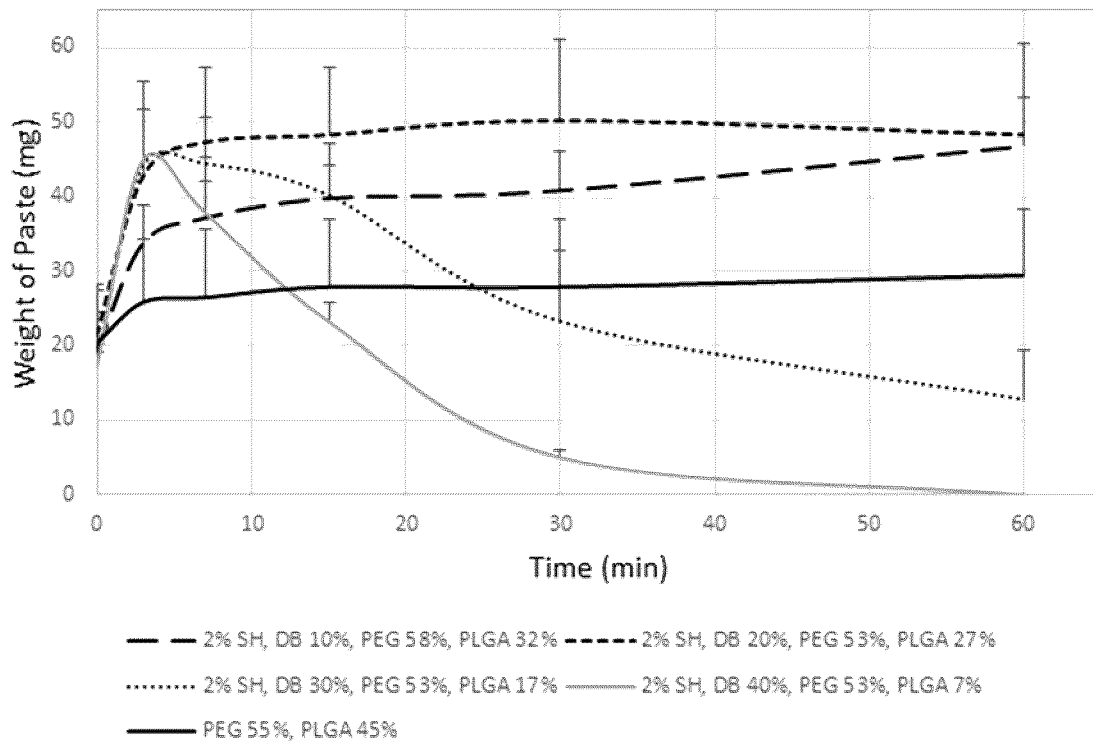
FIG. 23 shows the water absorption of pastes containing a swelling agent (i.e. 2% sodium hyaluronate (SH)) and variable amounts of diblock copolymer (i.e. 10%, 20%, 30% and 40%) as compared to no SH and no diblock.

As shown in FIG. 23, pastes with 2% SH were swelling rapidly after contact with water. Pastes with 0 and 10% of diblock absorbed less water than pastes with higher diblock copolymer content. Furthermore, these pastes did also not disintegrate over the monitored time. Pastes that contained 20, 30 and 40% diblock copolymer immediately absorbed water to roughly double their initial weight. The 20% paste hold its weight at least over one hour, whereas the 30% and 40% DB pastes lost 30 and 100% of their initial weight over one hour. Overall, a higher amount of DB allows for more rapid water absorption and swelling and quick paste disintegration.

Example 19

Release of Gemcitabine from Various Polymeric Pastes

Figure 24:
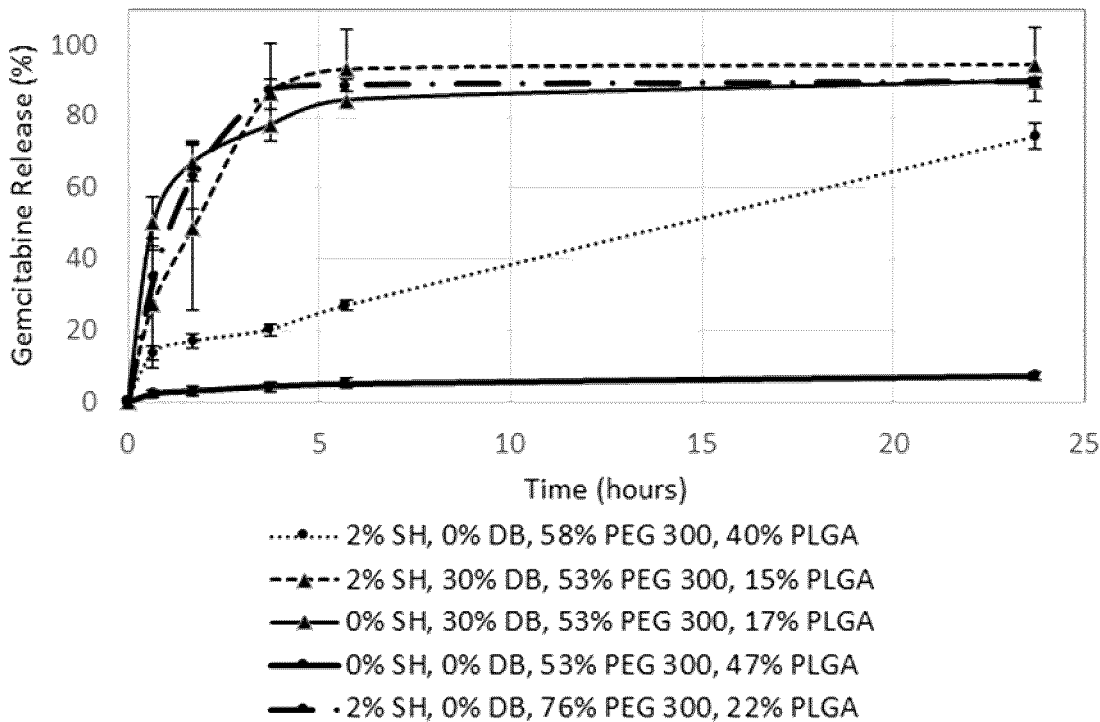
FIG. 24 shows the release of 5% Gemcitabine from pastes with (i.e. 2% sodium hyaluronate (SH)) and without swelling agent and with and without diblock copolymer. The pastes had a high PEG 300™ content (i.e. 53%, 58% and 76%).

As shown in FIG. 24, pastes having no diblock copolymer showed delayed release of gemcitabine, except where there was a high PEG 300 level (i.e. 76%) and low PLGA (i.e. 22%). All other compositions showed a burst release at between 0 and 4.5 hours and sustained release thereafter.

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. Numeric ranges are inclusive of the numbers defining the range. The word "comprising" is used herein as an open-ended term, substantially equivalent to the phrase "including, but not limited to", and the word "comprises" has a corresponding meaning. As used herein, the singular forms "a", "an" and "the" include plural referents unless the context clearly dictates otherwise. Thus, for example, reference to "a thing" includes more than one such thing. Citation of references herein is not an admission that such references are prior art to an embodiment of the present invention. The invention includes all embodiments and variations substantially as hereinbefore described and with reference to the examples and drawings.

REFERENCES

1. Schröder, F. H. et al. Screening and Prostate-Cancer Mortality in a Randomized European Study. *New England Journal of Medicine* 360, 1320-1328 (2009).

2. Crawford, E. D. et al. Comorbidity and Mortality Results From a Randomized Prostate Cancer Screening Trial. *Journal of Clinical Oncology* 29, 355-361 (2011).

3. Jung, J. W., Lee, J. K., Hong, S. K., Byun, S. S. & Lee, S. E. Stratification of patients with intermediate-risk prostate cancer. *BJU International* 115, 907-12 (2015).

4. Cooperberg, M. R. et al. Outcomes of active surveillance for men with intermediate-risk prostate cancer. *Journal of Clinical Oncology* 29, 228-34 (2011).

5. Klotz, L. et al. Clinical results of long-term follow-up of a large, active surveillance cohort with localized prostate cancer. *Journal of Clinical Oncology* 28, 126-31 (2010).

6. Hamdy, F. C. et al. 10-Year Outcomes after Monitoring, Surgery, or Radiotherapy for Localized Prostate Cancer. *New England Journal of Medicine* 375, 1415-1424 (2016).

7. Donovan, J. L. et al. Patient-Reported Outcomes after Monitoring, Surgery, or Radiotherapy for Prostate Cancer. *New England Journal of Medicine* 375, 1425-1437 (2016).

8. Eggener, S. et al. Focal therapy for prostate cancer: possibilities and limitations. *European Urology* 58, 57-64 (2010).

9. Ahmed, H. U. et al. Focal therapy for localized prostate cancer: a phase I/II trial. *Journal of Urology* 185, 1246-54 (2011).

10. Lindner, U. et al. Focal laser ablation for prostate cancer followed by radical prostatectomy: validation of focal therapy and imaging accuracy. *European Urology* 57, 1111-4 (2010).

11. Ritch, C. R. & Katz, A. E. Prostate cryotherapy: current status. *Curr Opin Urol* 19, 177-81 (2009).

12. Tsivian, M. & Polascik, T. J. Focal cryotherapy for prostate cancer. *Curr Urol Rep* 11, 147-51 (2010).

13. Lukka, H. et al. High-intensity focused ultrasound for prostate cancer: a systematic review. *Clinical Oncology* 23, 117-27 (2011).

14. Lughezzani, G. et al. Prognostic factors in upper urinary tract urothelial carcinomas: a comprehensive review of the current literature. *Eur Urol* 62, 100-14 (2012).

15. Audenet, F., Yates, D. R., Cussenot, O. & Roupret, M. The role of chemotherapy in the treatment of urothelial cell carcinoma of the upper urinary tract (UUT-UCC). *Urol Oncol* 31, 407-13 (2013).

16. Roupret, M. et al. European guidelines on upper tract urothelial carcinomas: 2013 update. *Eur Urol* 63, 1059-71 (2013).

17. Gitlitz, B. J. et al. A phase II study of gemcitabine and docetaxel therapy in patients with advanced urothelial carcinoma. *Cancer* 98, 1863-9 (2003).

18. Wesselmann, U., Burnett, A. L. & Heinberg, L. J. The urogenital and rectal pain syndromes. *Pain* 73, 269-294 (1997).

19. Granitsiotis, P. & Kirk, D. Chronic Testicular Pain: An Overview. *European Urology* 45, 430-436 (2004).

20. Strebel, R. T. et al. Chronic Scrotal Pain Syndrome: Management among Urologists in Switzerland. *European Urology* 47, 812-816 (2005).

21. Levine, L. A. & Hoeh, M. P. Evaluation and Management of Chronic Scrotal Content Pain. *Current Urology Reports* 16, 36 (2015).

22. Sinclair, A. M., Miller, B. & Lee, L. K. Chronic orchialgia: consider gabapentin or nortriptyline before considering surgery. *International Journal of Urology* 14, 622-5 (2007).

23. Davis, B. E., Noble, M. J., Weigel, J. W., Foret, J. D. & Mebust, W. K. Analysis and management of chronic testicular pain. *The Journal of Urology* 143, 936-939 (1990).

24. McJunkin, T. L., Wuollet, A. L. & Lynch, P. J. Sacral nerve stimulation as a treatment modality for intractable neuropathic testicular pain. *Pain Physician* 12, 991-5 (2009).

25. Basal, S. et al. A novel treatment of chronic orchialgia. *Journal of Andrology* 33, 22-6 (2012).

26. Khambati, A., Lau, S., Gordon, A. & Jarvi, K. A. OnabotulinumtoxinA (Botox) nerve blocks provide durable pain relief for men with chronic scrotal pain: a pilot open-label trial. *J Sex Med* 11, 3072-7 (2014).

27. Cui, T. & Terlecki, R. Prevalence of Relative Deficiencies in Testosterone and Vitamin B12 Among Patients Referred for Chronic Orchialgia: Implications for Management. *American Journal of Men's Health* (2016).

28. Polackwich, A. S. et al. Vasectomy Reversal for Postvasectomy Pain Syndrome: A Study and Literature Review. *Urology* 86, 269-272 (2015).

29. Hori, S., Sengupta, A., Shukla, C. J., Ingall, E. & McLoughlin, J. Long-Term Outcome of Epididymectomy for the Management of Chronic Epididymal Pain. *The Journal of Urology* 182, 1407-1412 (2009).

30. Lee, J. Y. et al. Efficacy of Epididymectomy in Treatment of Chronic Epididymal Pain: A Comparison of Patients With and Without a History of Vasectomy. *Urology* 77, 177-182 (2011).

31. Heidenreich, A., Olbert, P. & Engelmann, U. H. Management of Chronic Testalgia by Microsurgical Testicular Denervation. *European Urology* 41, 392-397 (2002).

32. Strom, K. H. & Levine, L. A. Microsurgical Denervation of the Spermatic Cord for Chronic Orchialgia: Long-Term Results From a Single Center. *The Journal of Urology* 180, 949-953 (2008).

33. Parekattil, S. J. & Gudeloglu, A. Robotic assisted andrological surgery. *Asian Journal of Andrology* 15, 67-74 (2013).

34. Oomen, R. J., Witjens, A. C., van Wijck, A. J., Grobbee, D. E. & Lock, T. M. Prospective double-blind preoperative pain clinic screening before microsurgical denervation of the spermatic cord in patients with testicular pain syndrome. *Pain* 155, 1720-6 (2014).

35. Marconi, M. et al. Microsurgical Spermatic Cord Denervation as a Treatment for Chronic Scrotal Content Pain: A Multicenter Open Label Trial. *The Journal of Urology* 194, 1323-1327 (2015).

36. Larsen, S. M., Benson, J. S. & Levine, L. A. Microdenervation of the Spermatic Cord for Chronic Scrotal Content Pain: Single Institution Review Analyzing Success Rate After Prior Attempts at Surgical Correction. *The Journal of Urology* 189, 554-558 (2013).

37. Engeler D., B. A. P., Borovicka J., Cotterell A., Dinis-Oliveira P., Elneil S., Hughes J., Messelink E. J., Van Ophoven A., Reisman Y., De C. Williams A. C. Guidelines on Chronic Pelvic Pain. *European Association of Urology* (2014).

38. Ciftci, H. et al. Evaluation of Sexual Function in Men with Orchialgia. *Archives of Sexual Behavior* 40, 631-634 (2011).

39. Levine, L. Chronic orchialgia: evaluation and discussion of treatment options. *Therapeutic Advances in Urology* 2, 209-214 (2010).

40. (2017).

41. Catterall, W. A. & Mackie, K. in Goodman & Gilman's: The Pharmacological Basis of Therapeutics, 12e (eds. Brunton, L. L., Chabner, B. A. & Knollmann, B. C.) (McGraw-Hill Education, New York, N.Y., 2011).

42. Benowitz, N. L. in Poisoning & Drug Overdose, 6e (ed. Olson, K. R.) (The McGraw-Hill Companies, New York, N.Y., 2012).

43. Bouissou, C., Rouse, J. J., Price, R. & van der Walle, C. F. The influence of surfactant on PLGA microsphere glass transition and water sorption: remodeling the surface morphology to attenuate the burst release. *Pharmaceutical Research* 23, 1295-305 (2006).

44. Jain, R. A. The manufacturing techniques of various drug loaded biodegradable poly(lactide-co-glycolide) (PLGA) devices. *Biomaterials* 21, 2475-2490 (2000).

45. Siegel, S. J. et al. Effect of drug type on the degradation rate of PLGA matrices. *European Journal of Pharmaceutics and Biopharmaceutics* 64, 287-293 (2006).

46. Makadia, H. K. & Siegel, S. J. Poly Lactic-co-Glycolic Acid (PLGA) as Biodegradable Controlled Drug Delivery Carrier. *Polymers* 3, 1377-1397 (2011).

47. Athanasiou, K. A., Niederauer, G. G. & Agrawal, C. M. Sterilization, toxicity, biocompatibility and clinical applications of polylactic acid/polyglycolic acid copolymers. *Biomaterials* 17, 93-102 (1996).

48. Dunn, R. L. in Modified-Release Drug Delivery Technology 647-655 (Informa Healthcare, 2002).

49. Jackson, J. K., Hung, T., Letchford, K. & Burt, H. M. The characterization of paclitaxel-loaded microspheres manufactured from blends of poly (lactic-co-glycolic acid) (PLGA) and low molecular weight diblock copolymers. *International Journal of Pharmaceutics* 342, 6-17 (2007).

50. Jackson, J. K. et al. Characterization of perivascular poly(lactic-co-glycolic acid) films containing paclitaxel. *International Journal of Pharmaceutics* 283, 97-109 (2004).

51. Jackson, J. K. et al. The Suppression of Human Prostate Tumor Growth in Mice by the Intratumoral Injection of a Slow-Release Polymeric Paste Formulation of Paclitaxel. *Cancer Research* 60, 4146-4151 (2000).

52. Winternitz, C. I., Jackson, J. K., Oktaba, A. M. & Burt, H. M. Development of a polymeric surgical paste formulation for taxol. *Pharmaceutical Research* 13, 368-75 (1996).

53. Zhang, X., Jackson, J. K. & Burt, H. M. Determination of surfactant critical micelle concentration by a novel fluorescence depolarization technique. *Journal of Biochemical and Biophysical Methods* 31, 145-150 (1996).

54. Jackson, J. K., Zhang, X., Llewellen, S., Hunter, W. L. & Burt, H. M. The characterization of novel polymeric paste formulations for intratumoral delivery. *International Journal of Pharmaceutics* 270, 185-198 (2004).

55. Zhang, X., Jackson, J. K. & Burt, H. M. Development of amphiphilic diblock copolymers as micellar carriers of taxol. *International Journal of Pharmaceutics* 132, 195-206 (1996).

What is claimed is:

1. A composition consisting of a mixture of the following components:
    (a) a hydrophobic water-insoluble polymer having an inherent viscosity (IV) of about 0.15 to about 0.5 dL/g;
    (b) a low molecular weight biocompatible glycol; with a molecular weight at or below 1,450 Daltons; and
    (c) one or more drug compounds or pharmaceutically acceptable salt, solvate or solvate of the salt thereof,
    wherein the components (a) and (b) do not form covalent bonds with each other, and the ratio of the low molecular weight biocompatible glycol to the hydrophobic water-insoluble polymer is between about 70%:30% and about 40%:60%.

2. The composition of claim 1, wherein the hydrophobic water-insoluble polymer having an inherent viscosity (IV) of about 0.15 to about 0.5 dL/g is polylactic-co-glycolic acid (PLGA).

3. The composition of claim 2, wherein the PLGA has a ratio of lactic acid (LA):glycolic acid (GA) at or below 75:25.

4. The composition of claim 1, wherein the hydrophobic water-insoluble polymer has an inherent viscosity (IV) of about 0.15 to about 0.3 dL/g.

5. The composition of claim 1, wherein the hydrophobic water-insoluble polymer has an inherent viscosity (IV) of about 0.15 to about 0.2.5 dL/g.

6. The composition of claim 1, wherein the low molecular weight biocompatible glycol has a molecular weight between about 76 Daltons and about 1,450 Daltons.

7. The composition of claim 1, wherein the low molecular weight biocompatible glycol is selected from Polyethylene glycol (PEG), methoxypolyethylene glycol (mePEG) and propylene glycol.

8. The composition of claim 1, wherein the low molecular weight biocompatible glycol is selected from PEG and mePEG.

9. The composition of claim 8, wherein the PEG or mePEG has an average molecular weight of between 300 Daltons and 1,450 Daltons.

10. The composition of claim 1, wherein the hydrophobic water-insoluble polymer having an inherent viscosity (IV) of about 0.15 to about 0.5 dL/g is PLGA having an LA:GA ratio of 50:50 and the low molecular weight biocompatible glycol is PEG or mePEG with a molecular weight of about 300 Daltons to about 1,450 Daltons.

11. The composition of claim 10, wherein the ratio of PEG or mePEG to PLGA is between about 60%40% and about 40%:60%.

12. The composition of claim 11, wherein the ratio of PEG or mePEG to PLGA is between about 60%:40% and about 50%:50%.

13. The composition of claim 1, wherein the low molecular weight biocompatible glycol is PEG 300.

14. The composition of claim 1, wherein the one or more drug compounds or pharmaceutically acceptable salt, solvate or solvate of the salt thereof is selected from one or more of the following categories: anti-cancer drugs; anti-inflammatory agents; anti-bacterial; anti-fibrotic; anesthetic; and analgesic.

15. The composition of claim 1, wherein the one or more drug compounds or pharmaceutically acceptable salt, solvate or solvate of the salt thereof is hydrophobic.

16. The composition of claim 1, wherein the one or more drug compounds or pharmaceutically acceptable salt, solvate or solvate of the salt thereof is hydrophilic.

17. The composition of claim 14, wherein the anti-cancer drug is selected from one or more of the following: Actinomycin; All-trans retinoic acid; Azacitidine; Azathioprine; Bleomycin; Bortezomib; Carboplatin; Capecitabine; Cisplatin; Chlorambucil; Cyclophosphamide; Cytarabine; Daunorubicin; Docetaxel; Doxifluridine; Doxorubicin; Epirubicin; Epothilone; Etoposide; Fluorouracil; Gemcitabine; Hydroxyurea; Idarubicin; Imatinib; Irinotecan; Mechlorethamine; Mercaptopurine; Methotrexate; Mitoxantrone; Oxaliplatin; Paclitaxel; Pemetrexed; Teniposide; Tioguanine; Topotecan; Valrubicin; Vemurafenib; Vinblastine; Vincristine; Vindesine; and Vinorelbine.

18. The composition of claim 14, wherein the anesthetic drug is a local anesthetic selected from one or more of the following: Procaine; Benzocaine; Chloroprocaine; Cocaine; Cyclomethycaine; Dimethocaine/Larocaine; Piperocaine; Propoxycaine; Procaine/Novocaine; Proparacaine; Tetracaine/Amethocaine; Articaine; Bupivacaine; Cinchocaine/Dibucaine; Etidocaine; Levobupivacaine; Lidocaine/Lignocaine/Xylocaine; Mepivacaine; Prilocaine; Ropivacaine; and Trimecaine.

* * * * *